United States Patent [19]
Scott et al.

[11] Patent Number: 6,096,773
[45] Date of Patent: *Aug. 1, 2000

[54] COMPOUNDS THAT INHIBIT THE BINDING OF INTEGRINS TO THEIR RECEPTORS

[75] Inventors: Ian L. Scott, Albany, N.Y.; Bore G. Raju, Fremont, Calif.; Ronald J. Biediger, Houston, Tex.; Vanessa O. Grabbe, Sugar Land, Tex.; Jamal Kassir; Karin M. Keller, both of Houston, Tex.; Timothy P. Kogan, deceased, late of Sugar Land, Tex., by Patricia Woodard Kogan, executrix; Shuqun Lin, Huntingdon Valley, Pa.; Robert V. Market, Pearland, Tex.

[73] Assignee: Texas Biotechnology Corporation, Inc., Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 09/292,459

[22] Filed: Apr. 15, 1999

Related U.S. Application Data

[60] Provisional application No. 60/082,019, Apr. 16, 1998.

[51] Int. Cl.[7] .......................... A61K 31/19; A61K 31/41; C07D 317/50; C07D 409/12
[52] U.S. Cl. .......................... 514/382; 514/444; 514/467; 514/512; 514/557; 548/252; 549/60; 549/74; 549/76; 549/78; 549/452; 549/550; 560/17; 560/22; 562/431; 564/163
[58] Field of Search ..................... 549/60, 452; 562/431; 514/444, 467, 512, 557, 382; 548/252

[56] References Cited

U.S. PATENT DOCUMENTS

| | | | |
|---|---|---|---|
| 4,372,974 | 2/1983 | Fish et al. | 424/319 |
| 5,192,746 | 3/1993 | Lobl et al. | 514/11 |
| 5,510,332 | 4/1996 | Kogan et al. | 514/14 |
| 5,654,301 | 8/1997 | Kohn et al. | 514/231.2 |

FOREIGN PATENT DOCUMENTS

| | | | |
|---|---|---|---|
| 0 341 915 | 5/1989 | European Pat. Off. | C07K 5/00 |
| 0 422 938 A1 | 11/1990 | European Pat. Off. | C07K 15/00 |
| WO 95/15973 | 6/1995 | WIPO | C07K 5/08 |
| WO 96/06108 | 2/1996 | WIPO | C07K 5/10 |
| WO 96/22966 | 8/1996 | WIPO | C07C 15/00 |
| 9804247 | 2/1998 | WIPO . | |
| WO 98/04247 | 2/1998 | WIPO | A61K 31/00 |
| WO 98/04913 | 2/1998 | WIPO | G01N 33/00 |

*Primary Examiner*—Joseph K. McKane
*Assistant Examiner*—Taofiq A. Solola
*Attorney, Agent, or Firm*—Rockey, Milnamow & Katz, Ltd.

[57] ABSTRACT

A method for the inhibition of the binding of $\alpha_4\beta_1$ integrin to its receptors, for example VCAM-1 (vascular cell adhesion molecule-1) and fibronectin; compounds that inhibit this binding; pharmaceutically active compositions comprising such compounds; and the use of such compounds either as above, or in formulations for the control or prevention of diseases states in which $\alpha_4\beta_1$ is involved.

10 Claims, No Drawings

COMPOUNDS THAT INHIBIT THE BINDING OF INTEGRINS TO THEIR RECEPTORS

CROSS-REFERENCE TO RELATED APPLICATION

This application is a continuation-in-part of co-pending U.S. Provisional Application No. 60/082019, filed Apr. 16, 1998.

FIELD OF THE INVENTION

This invention is directed generally to the inhibition of the binding of $\alpha_4\beta_1$ integrin to its receptors, for example VCAM-1 (vascular cell adhesion molecule-1) and fibronectin. The invention also relates to compounds that inhibit this binding; to pharmaceutically active compositions comprising such compounds; and to the use of such compounds either as above, or in formulations for the control or prevention of disease states in which $\alpha_4\beta_1$ is involved.

BACKGROUND OF THE INVENTION

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells recognize the invaded or damaged tissue, bind to the wall of the capillary and migrate through the capillary into the affected tissue. These events are mediated by a family of proteins called cell adhesion molecules.

There are three main types of white blood cells: granulocytes, monocytes and lymphocytes. The integrin $\alpha_4\beta_1$ (also called VLA-4 for very late antigen-4) is a heterodimeric protein expressed on the surface of monocytes, lymphocytes and two subclasses of granulocytes: eosinophils and basophils. This protein plays a key role in cell adhesion through its ability to recognize and bind VCAM-1 and fibronectin, proteins associated with the endothelial cells that line the interior wall of capillaries.

Following infection or damage of tissue surrounding a capillary, endothelial cells express a series of adhesion molecules, including VCAM-1, that are critical for binding the white blood cells that are necessary for fighting infection. Prior to binding to VCAM-1 or fibronectin, the white blood cells initially bind to certain adhesion molecules to slow their flow and allow the cells to "roll" along the activated endothelium. Monocytes, lymphocytes, basophils and eosinophils are then able to firmly bind to VCAM-1 or fibronectin on the blood vessel wall via the $\alpha_4\beta_1$ integrin. There is evidence that such interactions are also involved in transmigration of these white blood cells into the damaged tissue as well as the initial rolling event itself.

Although white blood cell migration to the site of injury helps fight infection and destroy foreign material, in many instances this migration can become uncontrolled, with white blood cells flooding to the scene, causing widespread tissue damage. Compounds capable of blocking this process, therefore, may be beneficial as therapeutic agents. Thus, it would be useful to develop inhibitors that would prevent the binding of white blood cells to VCAM-1 and fibronectin.

Some of the diseases that might be treated by the inhibition of $\alpha_4\beta_1$ binding include, but are not limited to, atherosclerosis, rheumatoid arthritis, asthma, allergy, multiple sclerosis, lupus, inflammatory bowel disease, graft rejection, contact hypersensitivity, and type I diabetes. In addition to being found on some white blood cells, $\alpha_4\beta_1$ is also found on various cancer cells, including leukemia, melanoma, lymphoma and sarcoma cells. It has been suggested that cell adhesion involving $\alpha_4\beta_1$ may be involved in the metastasis of certain cancers. Inhibitors of $\alpha_4\beta_1$ binding may, therefore, also be useful in the treatment of some forms of cancer.

The isolation and purification of a peptide which inhibits the binding of $\alpha_4\beta_1$ to a protein is disclosed in U.S. Pat. No. 5,510,332. Peptides which inhibit binding are disclosed in WO 95/15973, EP 0 341 915, EP 0 422 938 A1, U.S. Pat. No. 5,192,746 and WO 96/06108. Novel compounds which are useful for inhibition and prevention of cell adhesion and cell adhesion-mediated pathologies are disclosed in WO 96/22966, WO 98/04247 and WO 98/04913.

It is therefore an object of the invention to provide novel compounds which are inhibitors of $\alpha_4\beta_1$ binding, and pharmaceutical compositions including such novel compounds.

BRIEF SUMMARY OF THE INVENTION

The present invention is directed to compounds of formula I

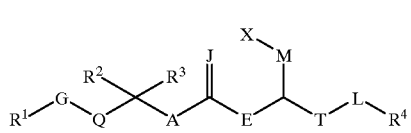

Formula I wherein A is selected from the group consisting of O, S, and $NR^5$;

E is selected from the group consisting of $CH_2$, O, S, and $NR^6$;

Q is selected from the group consisting of C(O) and $(CH_2)_k$ wherein k is an integer of 0 or 1;

J is selected from the group consisting of O, S and $NR^8$;

G is selected from the group consisting of O, NH, S, and $(CH_2)_p$ wherein p is an integer of 0 or 1;

T is selected from the group consisting of C(O) and $(CH_2)_b$ wherein b is an integer of from 0 to 3;

L is selected from the group consisting of O, $NR^7$, S, and $(CH_2)_n$ wherein n is an integer of 0 or 1;

M is selected from the group consisting of $C(R^9)(R^{10})$ and $(CH_2)_u$, wherein u is an integer of from 0 to 3;

X is selected from the group consisting of $CO_2B$, $PO_3H_2$, $SO_3H$, $OPO_3H_2$, $C(O)NHC(O)R^{11}$, $C(O)NHSO_2R^{12}$, tetrazolyl and hydrogen;

B, $R^1$, $R^2$, $R^3$, $R^4$, $R^5$, $R^6$, $R^7$, $R^8$, $R^9$, $R^{10}$, $R^{11}$ and $R^{12}$ are independently selected from the group consisting of hydrogen, alkyl, cycloalkyl, aryl, hydroxyalkyl, alkoxy, alkoxyalkoxy, cycloalkylalkyl, alkylamino, haloalkyl, alkylaryl, arylalkyl, heterocyclyl, heterocyclylalkyl and alkylheterocyclyl groups;

wherein $R^2$ and $R^3$ taken together may form a ring; $R^4$ and $R^7$ taken together may form a ring; $R^9$ and $R^{10}$ taken together may form a ring;

and salts and optical isomers thereof.

For Formula I, presently preferred compounds may have $R^1$, $R^2$ and $R^3$ independently as hydrogen, alkoxy, alkoxyalkoxy, aryl, alkylaryl, arylalkyl, heterocyclyl or alkyl; $R^4$ as aryl, alkylaryl, arylalkyl, heterocyclyl, alkylheterocyclyl or heterocyclylalkyl; X as $CO_2B$; and M as $C(R^9)(R^{10})$ wherein $R^9$ and $R^{10}$ are independently hydrogen or lower alkyl.

More specifically, the compounds of this invention may be described by Formula II Formula II

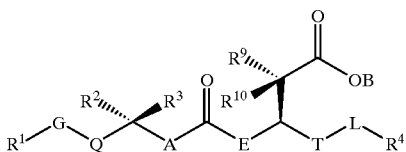

wherein the substituents are as defined for Formula I, and the pharmaceutically acceptable salts and prodrugs thereof.

For Formula II, presently preferred compounds may have $R^1$, $R^2$ and $R^3$ independently as hydrogen, alkoxy, alkoxyalkoxy, aryl, alkylaryl, arylalkyl, heterocyclyl or alkyl; $R^4$ as aryl, alkylaryl, arylalkyl, heterocyclyl, heterocyclylalkyl or alkyheterocyclyl; $R^5$ and $R^6$ if present as hydrogen; and $R^9$ and $R^{10}$ independently as hydrogen or lower alkyl.

Preferred compounds have the following substituents: $R^1$, $R^2$ and $R^3$ are independently selected from the group consisting of hydrogen, alkoxy, alkoxyalkoxy, aryl, alkylaryl, arylalkyl, heterocyclyl, alkylheterocyclyl, heterocyclylalkyl and alkyl; $R^4$ is selected from the group consisting of aryl, alkylaryl, arylalkyl, heterocyclylalkyl, alkylheterocyclyl and heterocyclyl; $R^5$ and $R^6$ if present are hydrogen; X is $CO_2B$ and B is independently selected from the group consisting of hydrogen and lower alkyl.

Presently preferred compounds are (3S)-3-(1,3-benzodioxol-5-yl)-3-(((((1S)-3-(methylsulfanyl)-1-((phenylsulfanyl)methyl)propyl)amino) carbonyl)amino) propanoic acid, (3S)-3-(1,3-benzodioxol-5-yl)-3-(((((1S)-2-((cyclopropylmethyl)thio)-1-((phenylthio)methyl)ethyl) amino)carbonyl) amino)propanoic acid, (9S,13S)-13-(1,3-benzodioxol-5-yl)-3,11-dioxo-1-phenyl-9-{[(2-thienylmethyl)amino]carbonyl}-2-oxa-4,10,12-triazapentadecan-15-oic acid, (9S,13S)-13-(1,3-benzodioxol-5-yl)-9-{[(3-hydroxy- 4-methoxybenzyl)amino]carbonyl}-3,11-dioxo-2-oxa-4,10,12-triazapentadecan-15-oic acid, (3S)-3-(1,3-benzodioxol-5-yl)-3-{[({(1S)-2-(benzylsulfanyl)-1-[(phenylsulfanyl)methyl]ethyl}amino)carbonyl]amino}propanoic acid, (3S)-3-(1,3-benzodioxol-5-yl)-3-{[({(1S)-3-(methylsulfanyl)-1-[({4-[(2-toluidinocarbonyl)amino]phenyl}sulfanyl) methyl]propyl}amino)carbonyl]amino}propanoic acid, (3S)-3-(1,3-benzodioxol-5-yl)-3-{[({(1S)-2-(ethylsulfanyl)-1-[(phenylsulfanyl)methyl]ethyl}amino) carbonyl]amino}propanoic acid, (9S,13S)-13-(1,3-benzodioxol-5-yl)-9-[({4-[(2-methylbenzyl)amino]benzyl}amino)carbonyl]-3,11-dioxo-1-phenyl-2-oxa-4,10,12-triazapentadecan-15-oic acid, (3S)-3-(1,3-benzodioxol-5-yl)-3-{[({(1S)-3-(methylsulfanyl)-1-[({3-[(2-toluidinocarbonyl)amino]phenyl}sulfanyl)methyl]propyl}amino)carbonyl] amino}propanoic acid, (3S)-3-(1,3-benzodioxol-5-yl)-3-{[({(1S)-2-(ethylthio)-1-[(phenylthio)methyl]ethyl}oxy) carbonyl]amino}propanoic acid, (9S, 13S)-13-(1,3-benxodioxol-5-yl)-3,11-dioxo-1-phenyl-9-(((4-((2-toluidinocarbonyl)amino)benzyl)amino)carbonyl)-2-oxa-4,10,12-triazapentadecan-15-oic acid and pharmaceutically acceptable salts, optical isomers and pro-drugs thereof.

The present invention also relates to pharmaceutical compositions comprising a physiologically acceptable diluent and at least one compound of the present invention.

The present invention further relates to a process of inhibiting the binding of $\alpha_4\beta_1$ integrin to VCAM-1 comprising exposure of a cell expressing $\alpha_4\beta_1$ integrin to a cell expressing VCAM-1 in the presence of an effective inhibiting amount of a compound of the present invention. The VCAM-1 may be on the surface of a vascular endothelial cell, an antigen presenting cell, or other cell type. The $\alpha_4\beta_1$ may be on a white blood cell such as a monocyte, lymphocyte, granulocyte; a stem cell; or any other cell that naturally expresses The invention also provides a method for treating disease states mediated by $\alpha_4\beta_1$ binding which comprises administration of an effective amount of a compound of the present invention, either alone or in formulation, to an afflicted patient.

DETAILED DESCRIPTION OF THE INVENTION

As used herein, the term "alkyl" means straight or branched, saturated or unsaturated carbon chains having up to 10, preferably up to 6 and more preferably up to 4 carbon atoms. As used herein, this term is meant to encompass alkenyl and alkynyl groups. "Lower alkyl" refers to $C_1$–$C_6$ alkyl.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantyl among others. As used herein, this term is meant to encompass alkenyl and alkynyl groups. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a cycloalkyl group appended to a lower alkyl radical, including, but not limited to cyclohexylmethyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy" as used herein refers to $R_aO$— wherein $R_a$ is a lower alkyl group. Examples of alkoxy include, but are not limited to, ethoxy, tert-butoxy, among others.

The term "alkoxyalkoxy" as used herein refers to $R_bO$—$RCO$— wherein $R_b$ is lower alkyl as defined above and $R_c$ is alkylene wherein alkylene is —$(CH_2)_n$— wherein n' is an integer from 1 to 6. Representative examples of alkoxyalkoxy groups include methoxymethoxy, ethoxymethoxy, t-butoxymethoxy, among others.

The term "alkylamino" as used herein refers to $R_dNH$— wherein $R_d$ is a lower alkyl group, for example, ethylamino, butylamino, among others. The term "carboxy" as used herein refers to a carboxylic acid radical, —C(O)OH.

The term "amino" as used herein refers to $H_2N$—.

As used herein, the term "aryl" means a carbocyclic aromatic group, as for example phenyl, naphthyl, indenyl, indanyl, anthracenyl, among others.

The term "heterocyclyl" refers to an aromatic or non-aromatic cyclic group having one or more oxygen, nitrogen or sulfur atoms in the ring, as for example, furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, indolinyl, benzo[b]furanyl, 2,3-dihydrobenzofuranyl, benzo[b]thiophenyl, 1H-indazolyl, benzimidazolyl, benzothiazolyl, purinyl, 4H-quinolizinyl, quinolinyl, isoquinolinyl, cinnolinyl, phthalazinyl, quinazolinyl, quinoxalinyl, 1,8- naphthyridinyl, pteridinyl, carbazolyl, acridinyl, phenazinyl, phenothiazinyl, and phenoxizinyl, tetrahydrofuranosyl, tetrahydropyranosyl, piperidinyl, piperazinyl, among others.

The term "heterocyclylalkyl" as used herein refers to a heterocyclyl group appended to a lower alkyl radical, including but not limited to 2-thienylmethyl, 2-pyridinylmethyl and 2-(1-piperidinyl) ethyl.

The term "alkylheterocyclyl" as used herein refers to an alkyl group appended to a heterocyclyl radical, including but not limited to 2-methyl-5-thiazolyl, 2-methyl-1-pyrrolyl and 5-ethyl-2-thiophenyl.

Suitable substituents for the aryl, alkyl, cycloalkyl, or heterocyclyl groups described above, when present, include alcohols, amines, heteroatoms, or any combination of aryl, alkoxy, alkoxyalkoxy, alkyl, cycloalkyl or heterocyclyl groups either attached directly, or via suitable linkers. The linkers are typically short chains of 1–3 atoms containing any combination of C, C=O, $CO_2$, O, N, or S, S=O, $SO_2$, as for example ethers, amides, amines, ureas, sulfamides, sulfonamides, among others.

For example, $R^1$, $R^2$ and $R^3$ in Formulas I and II above may independently be, but are not limited to, phenyl, thienylmethyl, isobutyl, n-butyl, 2-thienylmethyl, 1,3-thiazol-2-yl-methyl, benzyl, thienyl, 3-pyridinylmethyl, 3-methyl-1-benzothiophen-2-yl, allyl, isobutyl, 3-methoxybenzyl, propyl, 2-ethoxyethyl, cyclopropylmethyl, benzylsulfanylmethyl, benzylsulfonylmethyl, phenylsulfanylmethyl, phenethylsulfanylmethyl, 3-phenylpropylsulfanylmethyl, 4-((2-toluidinocarbonyl)amino)benzyl, 2-pyridinylethyl, 2-(1H-indol-3-yl)ethyl, 1H-benzimidazol-2-yl, 4-piperidinylmethyl, 3-hydroxy-4-methoxybenzyl, 4-hydroxyphenethyl, 4-aminobenzyl, phenylsulfonylmethyl, 4-(acetylamino)phenyl, 4-methoxyphenyl, 4-aminophenyl, 4-chlorophenyl, (4-(benzylsulfonyl)amino)phenyl, (4-(methylsulfonyl)amino) phenyl, 2-aminophenyl, 2-methylphenyl, isopropyl, isobutyl, 2-oxo-1-pyrrolidinyl, 3-(methylsulfanyl)propyl, (propylsulfanyl)methyl, octylsulfanylmethyl, 3-aminophenyl, 4-((2-toluidinocarbonyl)amino)phenyl, 2-((methylbenzyl)amino)benzyl, methylsulfanylethyl, or ethylsulfanylmethyl.

The $R^4$ substituent for formulas I and II above may be, but is not limited to 1,3-benzodioxol-5-yl, 1-naphthyl, thienyl, 4-isobutoxyphenyl, 2,6-dimethylphenyl, allyloxyphenyl, 3-bromo-4-methoxyphenyl, 4-butoxyphenyl, 1-benzofuran-2-yl, 2-thienylmethyl, phenyl, methylsulfanyl, phenylsulfanyl, phenethylsulfanyl, 4-bromo-2-thienyl, 3-methyl-2-thienyl, or 4,5-dihydro-1,3-oxazol-2-yl.

$R^2$ and $R^3$ may be linked to form a ring such as cyclopropyl, cyclopentyl, cyclobutyl, cyclohexyl, 4-piperidinyl, and 4-tetrahydropyranyl among others.

$R^4$ and $R^7$ may be linked to form a ring such 1-pyrrolidino, 1-piperidino, 4-methyl-1-piperazino, 4-acetyl-1-piperazino and 4-morpholino among others.

$R^9$ and $R^{10}$ may be linked to form a ring such as cyclopropyl, cyclobutyl, cyclopentyl, and cyclohexyl among others.

Abbreviations

Abbreviations which have been used in the schemes and the examples which follow are: BOC for t-butyloxycarbonyl; EtOAc for ethyl acetate; DMF for dimethylformamide; THF for tetrahydrofuran; Tos for p-toluenesulfonyl; DCC for dicyclohexylcarbodiimide; HOBT for 1-hydroxybenzotriazole; TFAA for trifluoroacetic anhydride; NMM for N-methyl morpholine; DIPEA for diisopropylethylamine; DCM for dichloromethane; CDI for 1,1'-carbonyldiimidazole; TBS for TRIS-buffered saline; EDCI for 1-(3-(dimethylamino)propyl-3-ethylcarbodiimide hydrochloride; Ms for methane sulfonyl and Cbz for benzyloxycarbonyl. Amino acids are abbreviated as follows: C for L-cysteine; D for L-aspartic acid; E for L-glutamic acid; G for glycine; H for L-histidine; I for L-isoleucine; L for L-leucine; N for L-asparagine; P for L-proline; Q for L-glutamine; S for L-serine; T for L-threonine; V for L-valine and W for L-tryptophan.

Examples of procedures that may be used to synthesize compounds of formula I are given in Schemes 1–4. A detailed description of the preparation of representative compounds of the present invention is set forth in the Examples below.

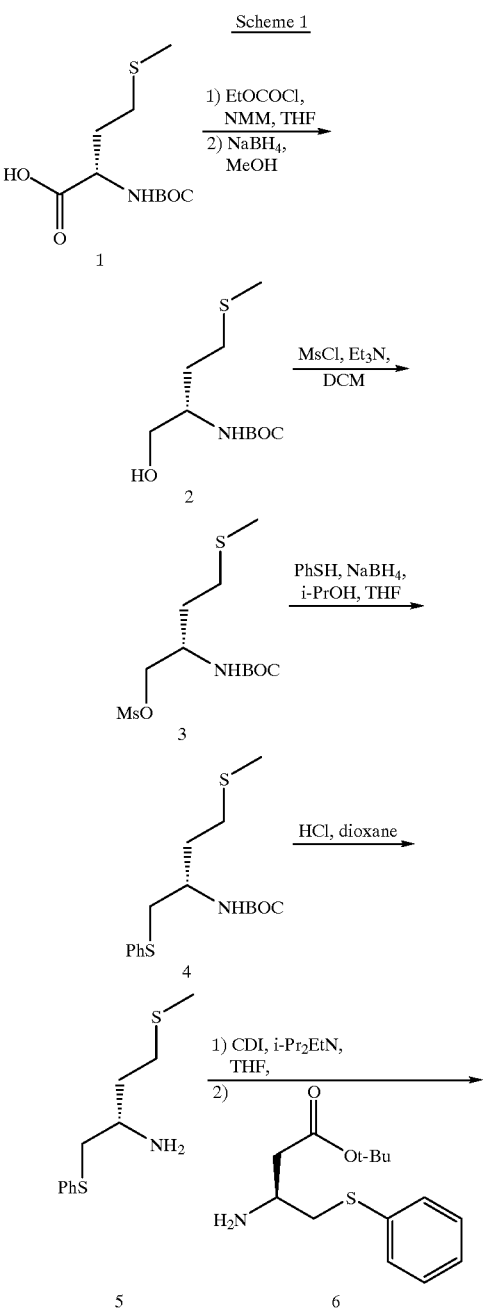

Scheme 1

7
-continued
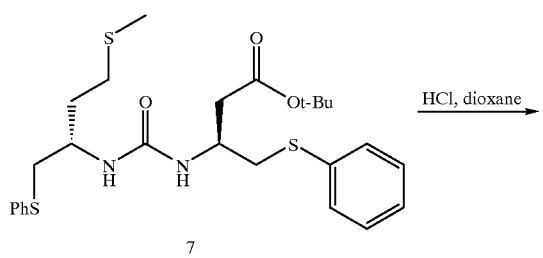
7
HCl, dioxane →
8
-continued
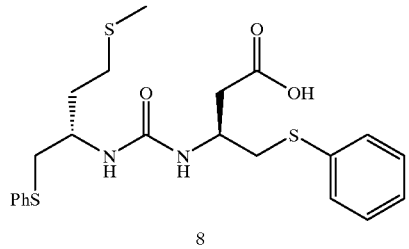
8
Scheme 2
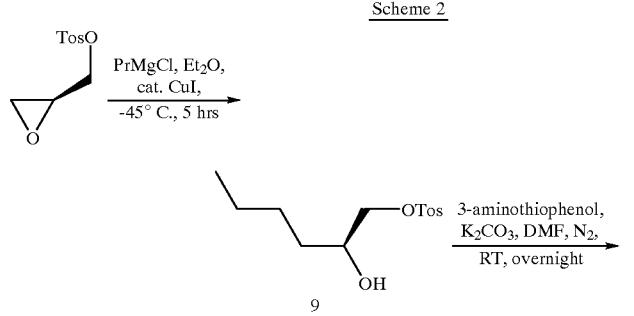

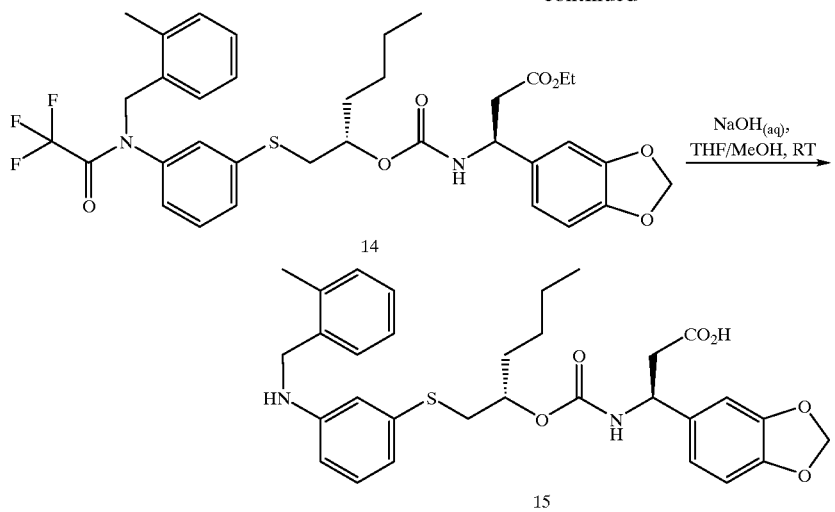
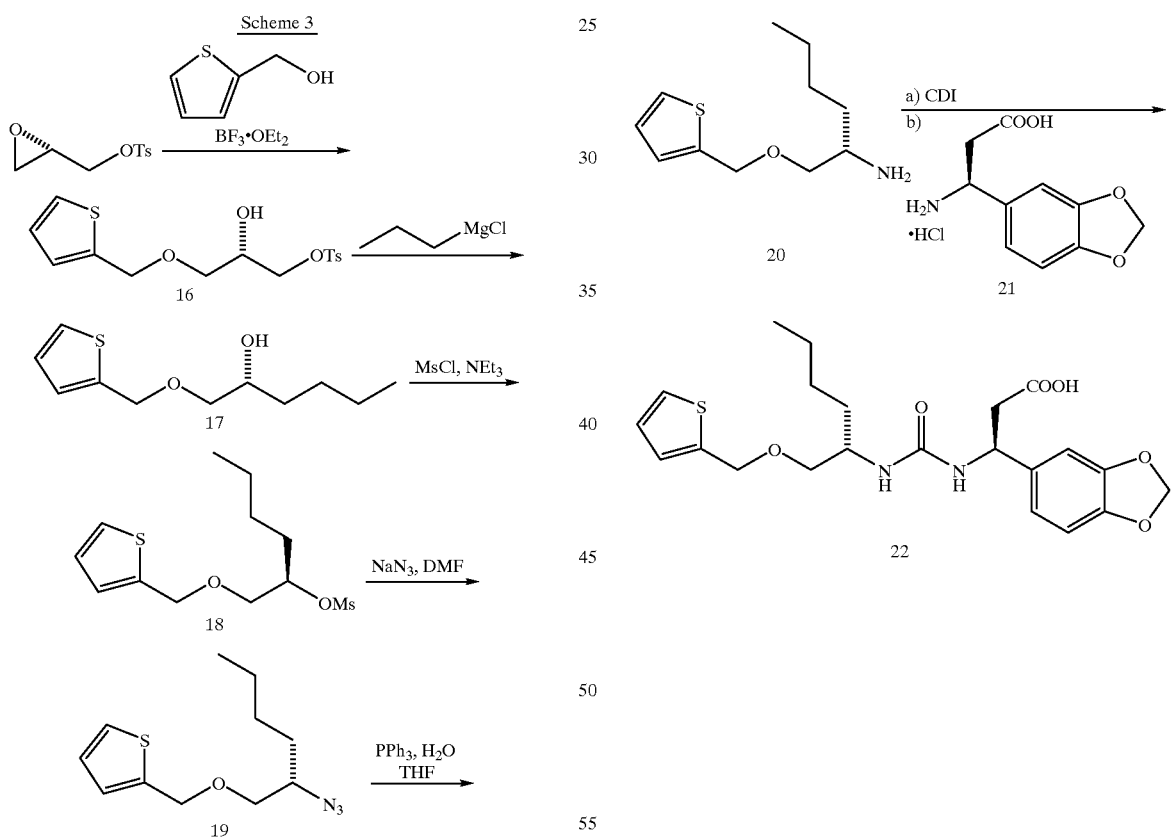

Scheme 4

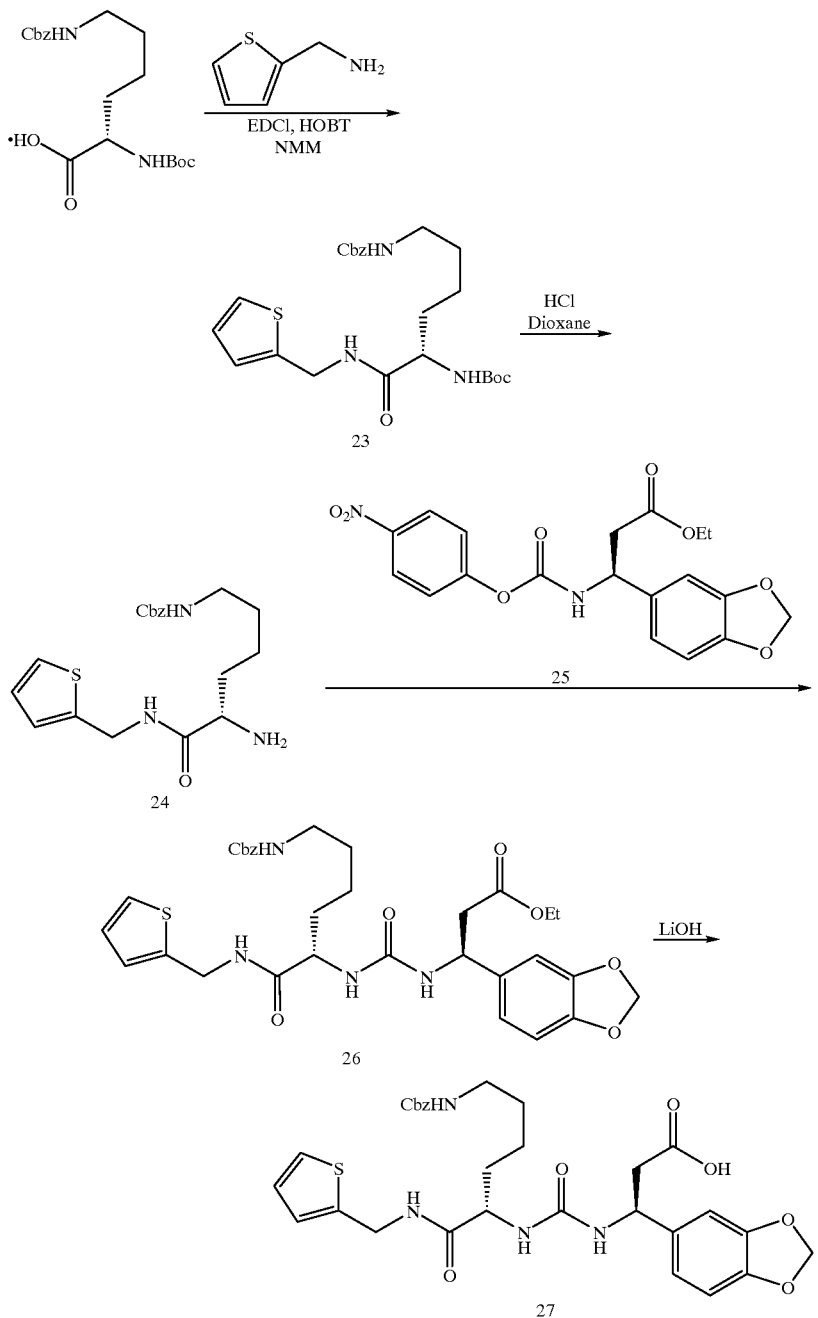

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quatemized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracistemally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrastemal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar—agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated formns for the purposes of the invention.

In another aspect, the present invention contemplates a process of inhibiting the binding of $\alpha_4\beta_1$ integrin to VCAM-1. A process of the present invention can be used either in vitro or in vivo. In accordance with a process of the present invention, a cell expressing $\alpha_4\beta_1$ integrin is exposed to a cell expressing VCAM-1 in the presence of an effective inhibiting amount of a compound of the present invention.

A cell expressing $\alpha_4\beta_1$ integrin can be a naturally occurring white blood cell, mast cell or other cell type that naturally expresses $\alpha_4\beta_1$ on the cell surface, or a cell transfected with an expression vector that contains a polynucleotide (e.g., genomic DNA or cDNA) that encodes $\alpha_4\beta_1$ integrin. In an especially preferred embodiment, $\alpha_4\beta_1$ integrin is present on the surface of a white blood cell such as a monocyte, a lymphocyte or a granulocyte (e.g., an eosinophil or a basophil).

A cell that expresses VCAM-1 can be a naturally occurring cell (e.g. an endothelial cell) or a cell transfected with an expression vector containing a polynucleotide that encodes VCAM-1. Methods for producing transfected cells that express VCAM-1 are well known in the art.

Where VCAM-1 exists on the surface of cell, the expression of that VCAM-1 is preferably induced by inflammatory cytokines such as tumor necrosis factor-$\alpha$, interleukin-4 and interleukin-1$\beta$.

Where the cells expressing $\alpha_4\beta_1$ integrin and VCAM-1 are in a living organism, a compound of the present invention is administered in an effective amount to the living organism. Preferably, the compound is in a pharmaceutical composition of this invention. A process of the present invention is especially useful in treating diseases associated with uncontrolled migration of white blood cells to damaged tissue. Such diseases include, but are not limited to, asthma, atherosclerosis, rheumatoid arthritis, allergy, multiple sclerosis, lupus, inflammatory bowel disease, graft rejection, contact hypersensitivity, type I diabetes, leukemia, and brain cancer. Administration is preferably accomplished via intravascular, subcutaneous, intranasal, transdermal or oral delivery.

The present invention also provides a process of selectively inhibiting the binding of $\alpha_4\beta_1$ integrin to a protein comprising exposing the integrin to the protein in the presence of an effective inhibiting amount of a compound of the present invention. In a preferred embodiment, the $\alpha_4\beta_1$ integrin is expressed on the surface of a cell, either naturally occurring or a cell transformed to express $\alpha_4\beta_1$ integrin.

The protein to which the $\alpha_4\beta_1$ integrin binds can be expressed either on a cell surface or be part of the extracellular matrix. Especially preferred proteins are fibronectin or invasin.

The ability of compounds of the present invention to inhibit binding is described in detail hereinafter in the Examples. These Examples are presented to describe preferred embodiments and utilities of the invention and are not meant to limit the invention unless otherwise stated in the claims appended hereto.

EXAMPLE 1

Synthesis of (3S)-3-{[({(1S)-3-(methylsulfanyl)-1-[(phenylsulfanyl)methyl]propyl)amino)carbonyl]amino}-4-(phenylsulfanyl)butanoic acid (8)

Step One:

N-Boc-L-Methionine 1 (2 g, 8 mmol) was dissolved in THF (40 mL) and the solution cooled to 0° C. N-Methylmorpholine (0.77 mL, 8 mmol) and ethyl chloroformate (0.88 ml, 8 mmol) were added and the mixture was stirred for 30 minutes while maintaining the low temperature. The mixture was quickly filtered and sodium borohydride (0.88 g, 23 mmol) was added. Methanol (100 mL) was added slowly to the ice-cold solution. The ice-bath was removed and the solution stirred at room temperature for 1 hour. A standard aqueous work-up gave the primary alcohol 2 (1.8 g, 95%).

Step Two:

To an ice-cold solution of the alcohol 2 (1.8 g, 7.7 mmol) in methylene chloride (30 mL) was added triethylamine (1.6 mL, 11.5 mmol) and methanesulfonyl chloride (0.8 mL, 10.4 mmol). After 5 minutes, the reaction was poured into water. A standard aqueous work-up gave the mesylate 3 (2.24 g, 93%).

Step Three:

To a solution of the mesylate 3 (1 g, 3.2 mmol) in a mixture of THF (10 mL) and isopropanol (10 ml) was added thiophenol (0.33 mL, 3.2 mmol) and sodium borohydride (0.15 g, 3.9 mmol). The mixture was stirred at room temperature overnight. A standard aqueous work-up gave the sulfide 4 (0.94 g, 90%).

Step Four:

To a solution of the sulfide 4 (0.94 g, 2.9 mmol) in 1,4-dioxane (3 mL) was added hydrochloric acid (3 mL, 4M: 1,4-dioxane) and the solution was stirred at room temperature for 4 hours. Nitrogen was bubbled through the solution to drive off most of the excess HCl. Concentration under reduced pressure, followed by high vacuum, gave the amine hydrochloride 5 (0.86 g). The excess weight was due to residual 1,4-dioxane.

Step Five:

A solution of the amine hydrochloride 5 (0.21 g, 0.8 mmol), and carbonyldiimidazole (0.15 g, 0.9 mmol) in methylene chloride (2 mL) was stirred at room temperature for 30 minutes. A solution of the amine 6 (prepared from Boc-L-Asp(OtBu)—OH following the above reaction sequence) (0.266 g, 0.9 mmol) in methylene chloride (1 mL) was added and the mixture was stirred first at room temperature overnight and then at 40° C. for 1 hour. A standard acid-base work-up, followed by purification by flash chromatography (silica:eluent 3:1–2:1 hexanes:ethyl acetate) gave the urea 7 (0.427 g, quant.).
Step Six:

To a solution of the urea 7 (0.328 g, 0.6 mmol) in 1,4-dioxane (1 mL) was added hydrochloric acid (1 mL, 4M: 1,4-dioxane) and the solution was stirred at room temperature overnight. A standard aqueous work-up, followed by flash chromatography (silica: chloroform—9:1 chloroform:methanol) gave the title compound 8 (0.065 g, 37%). $^1$H NMR: (400 MHz: DMSO-d$_6$) δ 1.63 (1H, m), 1.88 (1H, m), 2.01 (3H, s), 2.35–2.60 (4H, m), 2.97 (1H, dd), 3.06 (1H, dd), 3.12 (1H, dd), 3.17 (1H, dd), 3.82 (1H m), 4.06 (1H, br ddd), 6.01 (1H, d, NH), 6.14 (1H, d, NH), 7.17 (2H, m), 7.30 (4H, m), 7.38 (4H, m).

EXAMPLE 2

Synthesis of (3S)-3-(1,3-benzodioxol-5-yl)-3-{[({ (1S)-1-[({3-[(2-methylbenzyl)amino]phenyl}thio) methyl]pentyl}oxy)carbonyl]amino} propanoic acid (15)

Step One:

Copper (I) iodide (0.63 g, 3.3 mmol) was suspended in diethyl ether (100 mL) and chilled to −45° C. under nitrogen. n-Propylmagnesium chloride (16 mL, 1.0 M in diethyl ether, 16.0 mmol) was added slowly to the solution. After 10 minutes, (2S)-(+)-glycidyl tosylate (5.00 g, 21.9 mmol) in diethyl ether (100 mL) was added dropwise via cannula over 1 hour. After 5 hours, the mixture was warmed to 0° C. and quenched with saturated, aqueous ammonium chloride (50 mL). The mixture was diluted with water and extracted with ethyl acetate. The organic layer was washed with water and brine. The organic layer was dried over Na$_2$SO$_4$, filtered, and concentrated under reduced pressure. Compound 9 (5.61 g, 90%) was recovered as a clear oil and was used without further purification.

Step Two:

Compound 9 (1.55 g, 5.7 mmol) was dissolved in DMF (20.5 mL) at room temperature. Potassium carbonate (1.07 g, 7.7 mmol) was added and the suspension was sparged with nitrogen gas for 15 minutes. 3-Aminothiophenol (0.60 mL, 5.7 mmol) was introduced via syringe and the solution was stirred overnight. The mixture was diluted with water and ethyl acetate, and the pH of the aqueous layer was adjusted with dilute HCl to pH 5–6. The organic layer was washed with water and brine. The organic solution was dried over Na$_2$SO$_4$, filtered, and concentrated under reduced pressure. Compound 10 (1.25 g, 98%) was recovered as a yellow oil and was used without further purification.

Step Three:

Compound 10 (1.25 g, 5.7 mmol) and pyridine (1.3 mL, 15.9 mmol) were dissolved in dichloromethane (23.5 mL) and chilled to 0° C. The solution was treated with trifluoroacetic anhydride (2.0 mL, 14.1 mmol) and allowed to warm to room temperature overnight. The mixture was washed with 2N HCl, water and brine. The organic layer was dried over Na$_2$SO$_4$, filtered, and concentrated under reduced pressure. Compound 11 (2.05 g, 92%) was recovered as a yellow oil and was used without further purification.

Step Four:

Compound 11 (0.52 g, 1.25 mmol) was dissolved in acetone (5.5 mL). The resulting solution was treated with potassium carbonate and α-bromo-o-xylene (0.40 mL, 3.0 mmol) and refluxed overnight. The mixture was cooled and concentrated under reduced pressure. Purification by chromatography (silica gel, 4:1 hexanes:ethyl acetate) gave 12 (0.36 g, 69%).

Step Five:

Compound 12 (0.20 g, 0.51 mmol) was dissolved in THF (1.0 mL) and N,N-diisopropylethylamine (0.107 mL, 0.61 mmol) was added. The reaction mixture was chilled to 0° C. under nitrogen, and phosgene (0.32 mL, 20% in toluene) was added via syringe. The mixture was stirred 30 minutes at 0° C., then 2 hours at room temperature and then was recooled to 0° C. A solution of ethyl 3-amino-3-(3,4-methylenedioxyphenyl)propionate (13) (0.13 g, 0.56 mmol) and N,N-diisopropylethylamine (0.107 mL, 0.61 mmol) in THF (1.0 mL) was added by dropwise via cannula. The mixture was warmed to room temperature and stirred an additional 1 hour. The mixture was diluted with ethyl acetate and washed with 2N HCl, water and brine. The organic layer was dried over Na$_2$SO$_4$, filtered, and concentrated under reduced pressure. Purification by chromatography (silica gel, gradient elution 6:1 to 4:1 hexanes:ethyl acetate) gave 14 (0.19 g, 58%).

Step Six:

Compound 14 (0.19 g, 0.29 mmol) was dissolved in 3:1 THF/water (1.1 mL) and treated with 2N NaOH$_{(aq)}$ (0.3 mL, 0.6 mmol) and methanol (0.3 mL). After 1 hour at room temperature, the mixture was diluted with water and washed with dichloromethane. The ethyl acetate layer was acidified with excess 2N HCl and washed with ethyl acetate (2×). The organic layers were combined, washed with brine and dried over Na$_2$SO$_4$. The organic solution was filtered and concentrated under reduced pressure to give compound 15 (0.15 g, 94%). $^1$H NMR (400 MHz, DMSO-d$_6$): δ 7.62 (d, J=7.7 Hz, 1H), 7.26 (dd, 1H), 7.14 (m, 4H), 6.99 (dd, J=7.9 Hz, 1H), 6.87 (d, J=1.5 Hz, 1H), 6.79 (d, J=8.0 Hz 1H), 6.75 (dd, J=1.5, 8.0 Hz, 1H), 6.58 (br s, 1H), 6.53 (br d, J=7.3 Hz, 1H), 6.44 (br d, J=8.0 Hz, 1H), 5.96 (s, 2H), 4.83 (dd, J=8.0, 15.4 Hz, 1H), 4.67 (m, 1H), 4.21 (s, 2H), 3.0 (m, 2H), 2.63 (dd, J=8.3, 15.6 Hz, 1H), 2.56 (dd, J=6.6, 15.4 Hz 1H), 2.32 (s, 3H), 1.61 (m, 1H), 1.49 (m, 1H), 1.18 (m 4H), 0.78 (br, s, 3H).

EXAMPLE 3

Synthesis of (3S)-3-(1,3-benzodioxol-5-yl)-3-{[({ (1S)-1-[(2-thienylmethoxy)methyl]pentyl}amino) carbonyl]amino}propanoic acid (22)

Step One:

To a solution of (S)-glycidyl tosylate (842 mg, 3.69 mmol) and 2-thiophenemethanol (842 mg, 7.38 mmol) in CH$_2$Cl$_2$ (7.4 ml) cooled to 0° C. under a dry nitrogen atmosphere, BF$_3$•OEt$_2$ (0.046 ml, 0.37 mmol) was added by syringe. The mixture was warmed to room temperature and stirred 4 days, then concentrated under reduced pressure. The residue was purified by silica gel chromatography, eluting with 3:2 hexanes:ethyl acetate increasing to 1:1 hexanes:ethyl acetate to yield a 2:1 mixture of 16:(S)-glycidyl tosylate (394 mg) as a light yellow oil.

Step Two:

To a solution of a 2:1 mixture of 16:(S)-glycidyl tosylate (320 mg, assume 0.73 mmol 16 and 0.37 mmol (S)-glycidyl tosylate) in diethyl ether (22 ml) cooled to −78° C. under a dry nitrogen atmosphere, propylmagnesiumchloride (2.75 ml of a 2.0 M solution in diethyl ether, 5.5 mmol) was added dropwise by syringe. The resulting mixture was stirred at −78° C. for 15 minutes, then was allowed to warm to room temperature, stirred for 1 hour and quenched with saturated NH$_4$Cl. The mixture was diluted with ethyl acetate and washed with H$_2$O (2 times), and brine. The organic phase was dried over MgSO$_4$ and filtered and the filtrate was concentrated under reduced pressure. The residue was purified by silica gel chromatography, eluting with 3:1 hexanes:ethyl acetate to yield 17 (95 mg, 15% for two steps).

Step Three:

To a solution of 17 (116 mg, 0.54 mmol) in $CH_2Cl_2$ (3 ml) at room temperature under a dry nitrogen atmosphere, triethylamine (0.11 ml, 0.81 mmol) and methanesulfonyl chloride (0.053 ml, 0.68 mmol) were added dropwise by syringe. The resulting mixture was stirred for 15 minutes, was diluted with 1:1 hexanes:ethyl acetate and was washed with saturated $NaHCO_3$ and brine. The organic phase was dried over $MgSO_4$ and filtered and the filtrate was concentrated under reduced pressure to give 18 (153 mg) as a light yellow oil. This material was used without purification.

Step Four:

To a solution of 18 (150 mg, 0.51 mmol) in DMF (2 ml) cooled to 10° C. under a dry nitrogen atmosphere, sodium azide (66 mg, 1.0 mmol) was added. The resulting mixture was heated to 80° C. stirred for 2 hours, then was cooled to room temperature, diluted with 1:1 hexanes:ethyl acetate and washed with $H_2O$ (3 times) and brine. The organic phase was dried over $MgSO_4$ and filtered and the filtrate was concentrated under reduced pressure to give 19 (119 mg, 98%) as a light yellow oil. This material was used without purification.

Step Five:

To a solution of 19 (119 mg, 0.50 mmol) in THF (2 ml) at room temperature under a dry nitrogen atmosphere, $H_2O$ (0.092 ml, 5.1 mmol) and triphenylphosphine (401 mg, 1.53 mmol) were added. The resulting mixture was stirred for 44 hours at which time TLC indicated only partial conversion. Additional $H_2O$ (0.092 ml, 5.1 mmol) and triphenylphosphine (401 mg, 1.53 mmol) were added and the mixture was stirred for 4 days. The mixture was diluted with $CH_2Cl_2$ and was washed with approximately a 9:1 mixture of water/saturated $NaHCO_3$. The aqueous phase was extracted with $CH_2Cl_2$ (2 times) and the combined organic phases were dried over $MgSO_4$ and filtered. The filtrate was concentrated under reduced pressure and the resulting residue was purified by silica gel chromatography, eluting with 19:1 hexanes:ethyl acetate then 19:1 chloroform:methanol to yield 20 (75 mg, 70%) as a colorless oil.

Step Six:

To a solution of 20 (75 mg, 0.35 mmol) in 1,2-dichloroethane (2 ml) at room temperature under a dry nitrogen atmosphere, carbonyldiimidazole (62 mg, 0.38 mmol) was added. The resulting mixture was stirred for 2 hours and N,N-diisopropylethylamine (0.078 ml, 0.45 mmol) and 21 (101 mg, 0.41 mmol) were added. The mixture was heated to reflux for 14 hours, cooled to room temperature, then was diluted with ethyl acetate and was washed with HCl (2N) and brine. The organic phase was dried over $MgSO_4$ and filtered and the filtrate was concentrated under reduced pressure. The residue was purified by silica gel chromatography, eluting with 9:1 chloroform:methanol then 4:1 chloroform:methanol to yield 22 (70 mg, 45%) as a pale yellow powder. $^1$H NMR (400 MHz, $CD_3SOCD_3$): δ 0.81 (t, J=6.6 Hz, 3H), 1.22 (m, 5H), 1.45 (m, 1H), 2.39 (m, 2H), 3.37 (m, overlaps $H_2O$, 1H), 3.63 (m, 1H), 4.60 (d, J=12.8 Hz, 1H), 4.64 (d, J=12.8 Hz, 1H), 4.91 (m, 1H), 5.93 (s overlapping m, 3H), 6.61 (m, 1H), 6.75 (m, 3H), 6.84 (br. s, 1H), 7.02 (m, 2H), 7.49 (d, J=5.12 Hz, 1H).

EXAMPLE 4

Synthesis of (9S,13S)-13-(1,3-benzodioxol-5-yl)-3,11-dioxo-1-phenyl-9-{[(2-thienylmethyl)amino]carbonyl}-2-oxa-4,10,12-triazapentadecan-15-oic acid (27)

Step One:

N-α-t-BOC-N-ε-CBZ-L-Lysine (400.0 mg, 1.05 mmol) and thiophene 2-methylamine (0.12 ml, 1.16 mmol) were dissolved in DMF (7 ml). To this was added 1-(3-dimethylaminopropyl)-3 ethylcarbodiimide hydrochloride (222 mg, 1.16 mmol), 1-hydroxybenzotriazole (157.0 mg, 1.16 mmol), and 4-methylmorpholine (0.16 ml, 1.16 mmol). The reaction was then stirred at room temperature for 24 hours. The mixture was taken up in ethyl acetate (200 ml), washed with water (2×100 ml), a saturated solution of sodium bicarbonate (100 ml), brine (100 ml), dried over $MgSO_4$, and concentrated under reduced pressure to give compound 23 (451.7 mg, 90%), which was used without further purification.

Step Two:

Compound 23 (451 mg, 0.95 mmol) was dissolved in 2 N HCl in dioxane (6 ml) and stirred at room temperature for 2 hours. The mixture was concentrated under reduced pressure and the residue was taken up in ethyl acetate (150 ml) and a saturated solution of sodium bicarbonate (150 ml). The organic layer was separated, dried over $MgSO_4$, and concentrated under reduced pressure to yield compound 24 (306.9 mg, 94%), which was used without further purification.

Step Three:

Compound 24 (128 mg, 0.37 mmol) and compound 25 (150 mg, 0.37 mmol) were dissolved in tetrahydrofuran (3 ml). Triethylamine (0.05 ml, 0.37 mmol) was added and the reaction stirred at room temperature for 24 hours. The mixture was diluted with ethyl acetate (100 ml) and washed several times with 0.5 N aqueous NaOH (5×25 ml), dried over $MgSO_4$, and concentrated under reduced pressure to yield compound 26 (235.3 mg, 99%), which was used without any further purification.

Step Four:

Compound 26 (230 mg, 0.36 mmol) was dissolved in methanol (3 ml), water (3 ml), and tetrahydrofuran (3 ml) and to this solution was added lithium hydroxide (45 mg, 1.08 mmol). The reaction was heated to 50° C. and stirred for 24 hours. The mixture was concentrated under reduced pressure and the residue was taken up in ethyl acetate (100 ml) and 0.5 N aqueous HCl (50 ml). The organic layer was separated, dried over $MgSO_4$, and concentrated under reduced pressure to yield 171.1 mg (78%) of compound 27. $^1$H NMR(400 MHz, DMSO-$d_6$): δ 8.5–8.6 (m, 1H), 7.3–7.4 (m, 6H), 7.1–7.2 (m, 1H), 6.9–7.0 (m, 2H), 6.85 (s, 1H), 6.7–6.8 (m, 2H), 6.5–6.6 (m, 2H), 5.9 (s, 2H), 5.0 (s, 2H), 4.8–4.9 (m, 1H), 4.3–4.5 (m, 2H), 4.0–4.1 (m, 1H), 2.9–3.0 (m, 2H), 2.4 (m, 2H), 1.5–1.6 (m, 2H), 1.3–1.5 (m, 2H), 1.1–1.3 (m, 2H).

Synthetic procedures similar to those described above may be utilized to obtain the following compounds: 3-(1,3-benzodioxol-5-yl)-3-{[({(1R)-1-[(benzylsulfanyl)methyl]-2-methylpropyl}amino)carbonyl]amino}propanoic acid, 3-(1,3-benzodioxol-5-yl)-3-{[({(1S)-1-[(benzylsulfanyl)methyl]-2-methylpropyl}amino)carbonyl]amino}propanoic acid, 3-(1,3-benzodioxol-5-yl)-3-{[({(1S)-2-methyl-1-[(phenylsulfanyl)methyl]propyl}amino)carbonyl]amino}propanoic acid, 3-(1,3-benzodioxol-5-yl)-3-{[({(1S)-1-[(benzylsulfonyl)methyl]-2-methylpropyl}amino)carbonyl]amino}propanoic acid, 3-(1,3-benzodioxol-5-yl)-3-{[((1S)-1-{[(4-methoxybenzyl)amino]carbonyl}-3-methylbutyl)amino]carbonyl}amino)propanoic acid, 3-(1,3-benzodioxol-5-yl)-3-({[((1R)-1-{[(4-methoxybenzyl)amino]carbonyl}-3-methylbutyl)amino]carbonyl}amino) propanoic acid, (3R)-3-(1,3-benzodioxol-5-yl)-3-{[({(1S)-2-methyl-1-[(phenylsulfanyl)methyl]propyl}amino) carbonyl]amino}propanoic acid, (3S)-3-(1,3-benzodioxol-5-yl)-3-(((((1S)-2-methyl-1-((phenylsulfanyl)methyl) propyl)amino)carbonyl)amino)propanoic acid, (3S)-3-[({1-

{[bis-(phenylsulfanyl)]methyl}-2-methylpropyl] amino}carbonyl)amino]-3-[(3,4-methylenedioxy) phenyl] propanoic acid, (3S)-3-(1,3-benzodioxol-5-yl)-3-{[({(1S)-2-methyl-1-[(phenethylsulfanyl)methyl]propyl}amino) carbonyl]amino}propanoic acid, (3S)-3-(1,3-benzodioxol-5-yl)-3-({[((1S)-2-methyl-1-{[(3-phenylpropyl)sulfanyl] methyl}propyl)amino]carbonyl}amino)propanoic acid, (9S, 13S)-13-(1,3-benzodioxol-5-yl)-3,11-dioxo-1-phenyl-9-[({4-[(2-toluidinocarbonyl)amino]benzyl}amino)carbonyl]-2-oxa-4,10,12-triazapentadecan- 15-oic acid, (9S,13S)-13-(1,3-benzodioxol-5-yl)-9-{[(4-hydroxyphenethyl)amino] carbonyl}-3,11-dioxo-1-phenyl-2-oxa-4,10,12-triazapentadecan-15-oic acid, (9S,13S)-13-(1,3-benzodioxol-5-yl)-3,11-dioxo-1-phenyl-9-({[2-(2-pyridinyl)ethyl]amino}carbonyl)-2-oxa-4,10,12-triazapentadecan-15-oic acid, 3-(1,3-benzodioxol-5-yl)-3-{[({(1S)-3-methyl-1-[({4-[(2-toluidinocarbonyl)amino] benzyl}amino)carbonyl]butyl}amino) carbonyl] amino}propanoic acid, (3S)-3-(1,3-benzodioxol-5-yl)-3-(((((1S)-3-(methylsulfanyl)-1-((phenylsulfanyl)methyl) propyl)amino)carbonyl) amino)propanoic acid, (3S)-3-(1,3-benzodioxol-5-yl)-3-{[({(1S)-3-methyl-1-[(phenylsulfanyl) methyl]butyl}amino)carbonyl]amino}propanoic acid, (8S, 12S)-12-(1,3-benzodioxol-5-yl)-3,10-dioxo-8-((phenylsulfanyl)methyl)-2-oxa-4,9,11-triazatetradecan-14-oic acid, (9S,13S)-13-(1,3-benzodioxol-5-yl)-3,11-dioxo-9-[(phenylsulfanyl)methyl]-2-oxa-4,10,12-triazapentadecan-15-oic acid, (9S,13S)-13-(1,3-benzodioxol-5-yl)-3,11-dioxo-9-({[3-(2-oxo-1-pyrrolidinyl)propyl] amino}carbonyl)-1-phenyl-2-oxa-4,10,12-triazapentadecan-15-oic acid, (9S,13S)-13-(1,3-benzodioxol-5-yl)-9-({[2-(1H-indol-3-yl)ethyl] amino}carbonyl)-3,11-dioxo-2-oxa-4,10,12-triazapentadecan-15-oic acid, (9S,13S)-9-{[(1H-benzimidazol-2-ylmethyl)amino]carbonyl}-13-(1,3-benzodioxol-5-yl)-3,11-dioxo-2-oxa-4,10,12-triazapentadecan-15-oic acid, (9S,13S)-13-(1,3-benzodioxol-5-yl)-3,11-dioxo-9-{[(4-piperidinylmethyl) amino]carbonyl}-2-oxa-4,10,12-triazapentadecan-15-oic acid, (9S,13S)-13-(1,3-benzodioxol-5-yl)-3,11-dioxo-1-phenyl-9-{[(2-thienylmethyl)amino]carbonyl}-2-oxa-4,10, 12-triazapentadecan-15-oic acid, (9S,13S)-13-(1,3-benzodioxol-5-yl)-9-{[(3-hydroxy-4-methoxybenzyl) amino]carbonyl}-3,11-dioxo-2-oxa-4,10,12-triazapentadecan-15-oic acid, (9S,13S)-13-(1,3-benzodioxol-5-yl)-9-{[(4-hydroxyphenethyl)amino] carbonyl}-3,11-dioxo-2-oxa-4,10,12-triazapentadecan-15-oic acid, (9S,13S)-9-{[(4-aminobenzyl)amino]carbonyl}-13-(1,3-benzodioxol-5-yl)-3,11-dioxo-2-oxa-4,10,12-triazapentadecan-15-oic acid, (9S,13S)-13-(1,3-benzodioxol-5-yl)-3,11-dioxo-9-[(phenylsulfonyl)methyl]-2-oxa-4,10,12-triazapentadecan-15-oic acid, (9S,13S)-13-(1,3-benzodioxol-5-yl)-9-[({4-[bis(2-methylbenzyl)amino] benzyl}amino)carbonyl]-3,11-dioxo-2-oxa-4,10,12-triazapentadecan-15-oic acid, (3S)-3-[({[(1S)-1-({[4-(acetylamino)phenyl]sulfanyl}methyl)-3-(methylsulfanyl) propyl]amino}carbonyl)amino]-3-(1,3-benzodioxol-5-yl) propanoic acid, (3S)-3-(1,3-benzodioxol-5-yl)-3-[({[(1S)-1-{[(4-methoxyphenyl)sulfanyl]methyl}-3-(methylsulfanyl) propyl]amino}carbonyl) amino]propanoic acid, (3S)-3-[({ [(1S)-1-{[(4-aminophenyl)sulfanyl]methyl}-3-(methylsulfanyl)propyl]aminol}carbonyl)amino]-3-(1,3-benzodioxol-5-yl)propanoic acid, (3S)-3-(1,3-benzodioxol-5-yl)-3-[({[(1S)-1-{[(4-chlorophenyl)sulfanyl]methyl}-3-(methylsulfanyl)propyl]amino}carbonyl) amino]propanoic acid, (3S)-3-(1,3-benzodioxol-5-yl)-3-{[({(1S)-2-(benzylsulfanyl)-1-[(phenylsulfanyl)methyl]ethyl}amino) carbonyl]amino}propanoic acid, (3S)-3-(1,3-benzodioxol-5-yl)-3-[({[(1S)-1-[({4-[(benzylsulfonyl)amino] phenyl}sulfanyl)methyl]-3-(methylsulfanyl)propyl] amino}carbonyl)amino]propanoic acid, (3S)-3-(1,3-benzodioxol-5-yl)-3-{[({(1S)-3-(methylsulfanyl)-1-[({4-[(methylsulfonyl)amino]phenyl}sulfanyl)methyl] propyl}amino)carbonyl]amino}propanoic acid, (3S)-3-(1,3-benzodioxol-5-yl)-3-[({[(1S)-1-{[(4-{[(4-methylphenyl) sulfonyl]amino}phenyl)sulfanyl]methyl}-3-(methylsulfanyl)propyl]amino}carbonyl)amino]propanoic acid, 3-{[({(1S)-3-(methylsulfanyl)-1-[(phenylsulfanyl) methyl]propyl}amino)carbonyl]amino}propanoic acid, (3S)-3-(1,3-benzodioxol-5-yl)-3-{[({(1S)-3-(methylsulfanyl)-1-[({4-[(2-toluidinocarbonyl)amino] phenyl}sulfanyl) methyl]propyl}amino)carbonyl] amino}propanoic acid, (2S)-2-({[((1S)-5-{[(benzyloxy) carbonyl]amino}-1-{[(2-thienylmethyl)amino] carbonyl}pentyl) amino]carbonyl}amino)butanedioic acid, (3S)-3-(1,3-benzodioxol-5-yl)-3-{[({(1S)-2-(ethylsulfanyl)-1-[(phenylsulfanyl)methyl]ethyl}amino) carbonyl] amino}propanoic acid, (3S)-3-(1,3-benzodioxol-5-yl)-3-{[({(1S)-2-(methylsulfanyl)-1-[(phenylsulfanyl)methyl] ethyl}amino)carbonyl]amino}propanoic acid, N,N'-bis [(1S)-1-(1,3-benzodioxol-5-yl)-2-carboxyethyl]urea, (9S, 13S)-13-(1,3-benzodioxol-5-yl)-9-[({4-[( 2-methylbenzyl) amino]benzyl}amino)carbonyl]-3,11-dioxo-1-phenyl-2-oxa-4,10,12-triazapentadecan-15-oic acid, (3S)-3-(1,3-benzodioxol-5-yl)-3-(((((1R)-2-(benzylsulfonyl)-1-((phenylsulfanyl)methyl)ethyl)amino)carbonyl)amino) propanoic acid, (3S)-3-(1,3-benzodioxol-5-yl)-3-{[({(1S)-1-[(phenylsulfanyl)methyl]pentyl}amino) carbonyl] amino}propanoic acid, (3S)-3-(1,3-benzodioxol-5-yl)-3-[({ [(1S)-1-(1,3-benzodioxol-5-yl)-3-(tert-butoxy)-3-oxopropyl]amino}carbonyl) amino]propanoic acid, (3S)-3-[({[(1S)-1-{[(2-aminophenyl)sulfanyl]methyl}-3-(methylsulfanyl)propyl]amino}carbonyl)amino]-3-(1,3-benzodioxol-5-yl)propanoic acid, (3S)-3-(1,3-benzodioxol-5-yl)-3-[({[(1S)-1-{[(2-methylphenyl)sulfanyl]methyl}-3-(methylsulfanyl)propyl]amino}carbonyl)amino]propanoic acid, (3S)-3-(1,3-benzodioxol-5-yl)-3-[({[(1S)-1-{[(3-methylphenyl)sulfanyl]methyl}-3-(methylsulfanyl)propyl] amino}carbonyl)amino]propanoic acid, (3S)-3-(1,3-benzodioxol-5-yl)-3-(((2-(phenylsulfanyl)ethylamino) carbonyl)amino)propanoic acid, (3S)-3-(1,3-benzodioxol-5-yl)-3-{[({(1S)-2-[(3-phenylpropyl)sulfanyl]-1-[(phenylsulfanyl)methyl]ethyl}amino)carbonyl] amino}propanoic acid, (3S)-3-(1,3-benzodioxol-5-yl)-3-{ [({(1S)-2-(phenylsulfanyl)-1-[(propylsulfanyl)methyl] ethyl}amino)carbonyl]amino}propanoic acid, (3S)-3-(1,3-benzodioxol-5-yl)-3-{[({(1S)-3-(methylsulfanyl)-1-[(phenylsulfanyl)methyl]propyl}amino)carbothioyl] amino}propanoic acid, (3S)-4-(methylsulfanyl)-3-{[({(1S)-3-(methylsulfanyl)-1-[(phenylsulfanyl)methyl] propyl}amino)carbonyl]amino}butanoic acid, (3S)-3-{[({ (1S)-3-(methylsulfanyl)-1-[(phenylsulfanyl)methyl] propyl}amino)carbonyl]amino}-4-(phenylsulfanyl)butanoic acid, (3S)-3-(1,3-benzodioxol-5-yl)-3-[({[(1S)-1-methyl-2-(phenylsulfanyl)ethyl]amino}carbonyl)amino]propanoic acid, (3S)-3-(1,3-benzodioxol-5-yl)-3-{[({(1S)-2-(octylsulfanyl)-1-[(phenylsulfanyl)methyl]ethyl}amino) carbonyl]amino}propanoic acid, (3S)-3-(1,3-benzodioxol-5-yl)-3-{[({(1S)-3-(methylsulfanyl)-1-[({3-[(2-toluidinocarbonyl)amino]phenyl}sulfanyl)methyl] propyl}amino)carbonyl]amino}propanoic acid, (3S)-3-(1,3-benzodioxol-5-yl)-3-[({[(1S)-3-(methylsulfanyl)-1-(phenoxymethyl)propyl]amino}carbonyl) amino]propanoic acid, (3S)-3-(1,3-benzodioxol-5-yl)-3-{[({methyl{(1S)-3-

(methylsulfanyl)-1-[(phenylsulfanyl)methyl]propyl}amino) carbonyl]amino}propanoic acid, (3S)-3-(1,3-benzodioxol-5-yl)-3-{[({1-[(phenylsulfanyl)methyl]pentyl}oxy) carbonyl]amino}propanoic acid, (3S)-3-(1,3-benzodioxol-5-yl)-3-{[({2-(phenylsulfanyl)-1-[(phenylsulfanyl)methyl] ethyl}amino)carbonyl]amino}propanoic acid, (3S)-3-(1,3-benzodioxol-5-yl)-3-{[({(1S)-2-[(carboxymethyl)sulfanyl]-1-[(phenylsulfanyl)methyl]ethyl}amino)carbonyl] amino}propanoic acid, (3S)-3-[({[(1S)-1-{[(3-aminophenyl)thio]methyl}-3-(methylthio)propyl] amino}carbonyl)amino]-3-(1,3-benzodioxol-5-yl)propanoic acid, (3S)-3-(1,3-benzodioxol-5-yl)-3-[({[(1S)-1-[({4-[(2-methylbenzyl)amino]phenyl}thio)methyl]-3-(methylthio) propyl]amino}carbonyl)amino]propanoic acid, (3S)-3-(1,3-benzodioxol-5-yl)-3-[({[(1S)-1-[({3-[(methylsulfonyl) amino]phenyl}thio)methyl]-3-(methylthio)propyl] amino}carbonyl)amino]propanoic acid, (3S)-3-(1,3-benzodioxol-5-yl)-3-{[({(1S)-3-(methylthio)-1-[({3-[(propylsulfonyl)amino]phenyl}thio)methyl]propyl}amino) carbonyl]amino}propanoic acid, (3S)-3-{[({(1S)-2-(allyloxy)-1-[(phenylthio)methyl]ethyl}amino) carbonyl] amino}-3-(1,3-benzodioxol-5-yl)propanoic acid, (3S)-3-(1, 3-benzodioxol-5-yl)-3-{[({(1S)-2-(benzyloxy)-1-[(phenylthio)methyl]ethyl}amino)carbonyl] amino}propanoic acid, (3S)-3-(1,3-benzodioxol-5-yl)-3-[({ [(1R)-1-phenyl-2-(propylthio)ethyl]amino}carbonyl) amino]propanoic acid, (3S)-3-(1,3-benzodioxol-5-yl)-3-(((((1R)-1-benzyl-2-(propylthio)ethyl)amino)carbonyl) amino)propanoic acid, (3S)-3-(1,3-benzodioxol-5-yl)-3-{[({ (1S)-3-(phenylthio)-1-[(phenylthio)methyl]propyl}amino) carbonyl]amino}propanoic acid, (3S)-3-(1,3-benzodioxol-5-yl)-3-{[({(1S)-4-hydroxy-1-[(phenylthio)methyl] butyl}amino)carbonyl]amino}propanoic acid, (3S)-3-(1,3-benzodioxol-5-yl)-3-{[({(1S)-2-ethoxy-1-[(phenylthio) methyl]ethyl}oxy)carbonyl]amino}propanoic acid, (3S)-3-(1,3-benzodioxol-5-yl)-3-{[({(1S)-2-(phenethyloxy)-1-[(phenylthio)methyl]ethyl}oxy)carbonyl] amino}propanoic acid, (3S)-3-(1,3-benzodioxol-5-yl)-3-{ [({(1S)-2-[(cyclopropylmethyl)thio]-1-[(phenylthio) methyl]ethyl}amino)carbonyl]amino}propanoic acid, (3S)-3-(1,3-benzodioxol-5-yl)-3-{[({(1R)-2-(benzyloxy)-1-[(benzylthio)methyl]ethyl}amino)carbonyl] amino}propanoic acid, (3S)-3-(1,3-benzodioxol-5-yl)-3-{ [({(1R)-2-(benzyloxy)-1-[(benzylthio)methyl]ethyl}oxy) carbonyl]amino}propanoic acid, (3S)-3-(1,3-benzodioxol-5-yl)-3-{[({(1R)-2-(benzyloxy)-1-[(ethylthio)methyl] ethyl}oxy)carbonyl]amino}propanoic acid, (3S)-3-(1,3-benzodioxol-5-yl)-3-{[({(1S)-2-(ethylthio)-1-[(phenylthio) methyl]ethyl}oxy)carbonyl]amino}propanoic acid, (3S)-3-(1,3-benzodioxol-5-yl)-3-{[({(1S)-2-(benzylthio)-1-[(phenylthio)methyl]ethyl}oxy)carbonyl]amino}propanoic acid, (3S)-3-(1,3-benzodioxol-5-yl)-3-{[({(1S)-1-[({4-[(2-toluidinocarbonyl)amino]phenyl}thio)methyl]pentyl}oxy) carbonyl]amino}propanoic acid, (3S)-3-(1,3-benzodioxol-5-yl)-3-{[({(1S)-1-[({3-[(2-methylbenzyl)amino] phenyl}thio)methyl]pentyl}oxy)carbonyl]amino}propanoic acid, (3S)-3-(1,3-benzodioxol-5-yl)-3-{[({(1S)-2-{[(4-methylphenyl)sulfonyl]amino}-1-[(phenylthio)methyl] ethyl}amino) carbonyl]amino}propanoic acid, (3S)-3-(1,3-benzodioxol-5-yl)-3-{[({(1S)-1-[(2-thienylmethoxy) methyl]pentyl}amino)carbonyl]amino}propanoic acid, and pharmaceutically acceptable salts thereof.

EXAMPLE 5

A procedure in which a 26-amino acid peptide containing the CS1 sequence of fibronectin with an N-terminal Cys (CDELPQLVTLPHPNLHGPEILDVPST) was coupled to maleimide activated ovalbumin was used to determine the efficacy of the compounds synthesized. Bovine serum albumin (BSA) and CS1 conjugated ovalbumin were coated onto 96-well polystyrene plates at 0.5 $\mu$g/ml in TBS (50 mM TRIS, pH 7.5; 150 mM NaCl) at 4° C. for 16 hours. The plates were washed three times with TBS and blocked with TBS containing 3% BSA at room temperature for 4 hours. Blocked plates were washed three times in binding buffer (TBS; 1 mM $MgCl_2$; 1 mM $CaCl_2$; 1 mM $MnCl_2$) prior to assay. Ramos cells fluorescently labeled with calcein AM were resuspended in binding buffer ($10^7$ cells/ml) and diluted 1:2 with same buffer with or without compound. 100 $\mu$M of compound was added. The cells were added immediately to the wells (2.5×$10^5$ cells/well) and incubated for 30 minutes at 37° C. Following three washes with binding buffer, adherent cells were lysed and quantitated using a fluorometer. The results are shown in Table 1. $IC_{50}$ is defined as the dose required to give 50% inhibition. A stands for inhibition in Table 1, and the percent inhibition indicates the inhibition of cell adhesion when compound is included in the assay at a concentration of 100 $\mu$m. The lower the $IC_{50}$ value and the greater the percentage of inhibition, the more efficient the compound is at prevention of cell adhesion.

TABLE 1

| Compound | $IC_{50}$ | % A |
|---|---|---|
| 3-(1,3-benzodioxol-5-yl)-3-{[({(1R)-1-[(benzylsulfanyl)methyl]-2-methylpropyl} amino)carbonyl]amino}propanoic acid | 40 | 83 |
| 3-(1,3-benzodioxol-5-yl)-3-{[({(1S)-1-[benzylsulfanyl)methyl]-2-methylpropyl} amino)carbonyl]amino}propanoic acid | 10 | 100 |
| 3-(1,3-benzodioxol-5-yl)-3-{[({(1S)-2-methyl-1-[(phenylsulfanyl)methyl]propyl} amino)carbonyl]amino}propanoic acid | 5 | 99 |
| 3-(1,3-benzodioxol-5-yl)-3-{[({(1S)-1-[(benzylsulfonyl)methyl]-2-methylpropyl} amino)carbonyl]amino}propanoic acid | 35 | 92 |
| 3-(1,3-benzodioxol-5-yl)-3-({[((1S)-1-{[(4-methoxybenzyl)amino]carbonyl}-3-methyl butyl)amino]carbonyl}amino)propanoic acid | 0.5 | 100 |
| 3-(1,3-benzodioxol-5-yl)-3-({[((1R)-1-{[(4-methoxybenzyl)amino]carbonyl}-3-methyl butyl)amino]carbonyl}amino)propanoic acid | 45 | 66 |
| (3R)-3-(1,3-benzodioxol-5-yl)-3-{[({(1S)-2-methyl-1-[(phenylsulfanyl)methyl]propyl} amino)carbonyl]amino}propanoic acid | 35 | 83 |
| (3S)-3-(1,3-benzodioxol-5-yl)-3-(((((1S)-2-methyl-1-((phenylfulfanyl)methyl)propyl) amino)carbonyl)amino)propanoic acid | 2.5 | 100 |
| (3S)-3-[({[1-{[bis-(phenylsulfanyl)]methyl}-2-methylpropyl]amino}carbonyl)amino]-3-[(3,4-methylenedioxy)phenyl]propanoic acid | 35 | 95 |
| (3S)-3-(1,3-benzodioxol-5-yl)-3-{[({(1S)-2-methyl-1-[(phenethylsulfanyl)methyl] propyl}amino)carbonyl]amino}propanoic acid | 20 | 98 |

TABLE 1-continued

| Compound | IC$_{50}$ | % A |
|---|---|---|
| (3S)-3-(1,3-benzodioxol-5-yl)-3-({[((1S)-2-methyl-1-{[(3-phenylpropyl)sulfanyl]methyl}propyl)amino]carbonyl}amino)propanoic acid | 20 | 99 |
| (9S,13S)-13-(1,3-benzodioxol-5-yl)-3,11-dioxo-1-phenyl-9-[({4-[(2-toluidinocarbonyl)amino]benzyl}amino)carbonyl]-2-oxa-4,10,12-triazapentadecan-15-oic acid | 0.0003 | 100 |
| (9S,13S)-13-(1,3-benzodioxol-5-yl)-9-{[((4-hydroxyphenethyl)amino]carbonyl}-3,11-dioxo-1-phenyl-2-oxa-4,10,12-triazapentadecan-15-oic acid | 2 | 100 |
| (9S,13S)-13-(1,3-benzodioxol-5-yl)-3,11-dioxo-1-phenyl-9-({[2-(2-pyridinyl)ethyl]amino}carbonyl)-2-oxa-4,10,12-triazapentadecan-15-oic acid | 2 | 100 |
| 3-(1,3-benzodioxol-5-yl)-3-{[({(1S)-3-methyl-1-[({4-[(2-toluidinocarbonyl)amino]benzyl}amino)carbonyl]butyl}amino)carbonyl]amino}propanoic acid | 0.02 | 100 |
| (9S,13S)-13-(1,3-benzodioxol-5-yl)-9-({[2-(1H-indol-3-yl)ethyl]amino}carbonyl)-3,11-dioxo-2-oxa-4,10,12-triazapentadecan-15-oic acid | 45 | 78 |
| (3S)-3-(1,3-benzodioxol-5-yl)-3-{[({(1S)-3-methyl-1-[(phenylsulfanyl)methyl]butyl}amino)carbonyl]amino}propanoic acid | 2 | 100 |
| (3S)-3-(1,3-benzodioxol-5-yl)-3-(((((1S)-3-(methylsulfanyl)-1-((phenylsulfanyl)methyl)propyl)amino)carbonyl)amino)propanoic acid | 0.3 | 100 |
| (9S,13S)-13-(1,3-benzodioxol-5-yl)-3,11-dioxo-9-[(phenylsulfanyl)methyl]-2-oxa-4,10,12-triazapentadecan-15-oic acid | 0.4 | 100 |
| (8S,12S)-12-(1,3-benzodioxol-5-yl)-3,10-dioxo-8-((phenylsulfanyl)methyl)-2-oxa-4,9,11-triazatetradecan-14-oic acid | 2 | 100 |
| (9S,13S)-13-(1,3-benzodioxol-5-yl)-3,11-dioxo-9-({[3-(2-oxo-1-pyrrolidinyl)propyl]amino}carbonyl)-1-phenyl-2-oxa-4,10,12-triazapentadecan-15-oic acid | 3 | 100 |
| (9S,13S)-13-(1,3-benzodioxol-5-yl)-9-({[2-(1H-indol-3-yl)ethyl]amino}carbonyl)-3,11-dioxo-2-oxa-4,10,12-triazapentadecan-15-oic acid | 3.5 | 100 |
| (9S,13S)-9-{[(1H-benzimidazol-2-ylmethyl)amino]carbonyl}-13-(1,3-benzodioxol-5-yl)-3,11-dioxo-2-oxa-4,10,12-triazapentadecan-15-oic acid | 2 | 100 |
| (9S,13S)-13-(1,3-benzodioxol-5-yl)-3,11-dioxo-9-{[(4-piperidinylmethyl)amino]carbonyl}-2-oxa-4,10,12-triazapentadecan-15-oic acid | 5 | 97 |
| (9S,13S)-13-(1,3-benzodioxol-5-yl)-3,11-dioxo-1-phenyl-9-{[(2-thienylmethyl)amino]carbonyl}-2-oxa-4,10,12-triazapentadecan-15-oic acid, 27 | 0.2 | 100 |
| (9S,13S)-13-(1,3-benzodioxol-5-yl)-9-{[(3-hydroxy-4-methoxybenzyl)amino]carbonyl}-3,11-dioxo-2-oxa-4,10,12-triazapentadecan-15-oic acid | 0.2 | 100 |
| (9S,13S)-13-(1,3-benzodioxol-5-yl)-9-{[(4-hydroxyphenethyl)amino]carbonyl}-3,11-dioxo-2-oxa-4,10,12-triazapentadecan-15-oic acid | 6 | 100 |
| (9S,13S)-9-{[(4-aminobenzyl)amino]carbonyl}-13-(1,3-benzodioxol-5-yl)-3,11-dioxo-2-oxa-4,10,12-triazapentadecan-15-oic acid | 0.3 | 100 |
| (9S,13S)-13-(1,3-benzodioxol-5-yl)-3,11-dioxo-9-[(phenylsulfonyl)methyl]-2-oxa-4,10,12-triazapentadecan-15-oic acid | >100 | 20 |
| (9S,13S)-13-(1,3-benzodioxol-5-yl)-9-[({4-[bis(2-methylbenzyl)amino]benzyl}amino)carbonyl]-3,11-dioxo-2-oxa-4,10,12-triazapentadecan-15-oic acid | 1 | 95 |
| (3S)-3-[({[(1S)-1-({[4-(acetylamino)phenyl]sulfanyl}methyl)-3-(methylsulfanyl)propyl]amino}carbonyl)amino]-3-(1,3-benzodioxol-5-yl)propanoic acid | 3 | 100 |
| (3S)-3-(1,3-benzodioxol-5-yl)-3-[({[(1S)-1-{[(4-methoxyphenyl)sulfanyl]methyl}-3-(methylsulfanyl)propyl]amino}carbonyl)amino]propanoic acid | 7 | 100 |
| (3S)-3-[({[(1S)-1-{[(4-aminophenyl)sulfanyl]methyl}-3-(methylsulfanyl)propyl]amino}carbonyl)amino]-3-(1,3-benzodioxol-5-yl)propanoic acid | 3 | 100 |
| (3S)-3-(1,3-benzodioxol-5-yl)-3-[({[(1S)-1-{[(4-chlorphenyl)sulfanyl]methyl}-3-(methylsulfanyl)propyl]amino}carbonyl)amino]propanoic acid | 3 | 100 |
| (3S)-3-(1,3-benzodioxol-5-yl)-3-{[({(1S)-2-(benzylsulfanyl)-1-[(phenylsulfanyl)methyl]ethyl}amino)carbonyl]amino}propanoic acid | 0.02 | 100 |
| (3S)-3-(1,3-benzodioxol-5-yl)-3-[({[(1S)-1-[{4-[(benzylsulfonyl)amino]phenyl}sulfanyl)methyl]-3-(methylsulfanyl)propyl]amino}carbonyl)amino]propanoic acid | 0.3 | 100 |
| (3S)-3-(1,3-benzodioxol-5-yl)-3-{[({(1S)-3-(methylsulfanyl)-1-[({4-[(methylsulfonyl)amino]phenyl}sulfanyl)methyl]propyl}amino)carbonyl]amino}propanoic acid | 0.5 | 100 |
| (3S)-3-(1,3-benzodioxol-5-yl)-3-[({[(1S)-1-{[(4-{[(4-methylphenyl)sulfonyl]amino}phenyl)sulfanyl]methyl}-3-(methylsulfanyl)propyl]amino}carbonyl)amino]propanoic acid | 0.4 | 100 |
| 3-{[({(1S)-3-(methylsulfanyl)-1-[(phenylsulfanyl)methyl]propyl}amino)propanoic amino}propanoic acid | 25 | 96 |
| (3S)-3-(1,3-benzodioxol-5-yl)-3-{[({(1S)-3-(methylsulfanyl)-1-[({4-[(2-toluidinocarbonyl)amino]phenyl}sulfanyl)methyl]propyl}amino)carbonyl]amino}propanoic acid | 0.0009 | 100 |
| (2)-2-({[(((1S)-5-{[(benzyloxy)carbonyl]amino}-1-{[(2-thienylmethyl)amino]carbonyl}pentyl)amino}carbonyl}amino)butanedioic acid | 45 | 89 |
| (3S)-3-(1,3-benzodioxol-5-yl)-3-{[({(1S)-2-(ethylsulfanyl)-1-[(phenylsulfanyl)methyl]ethyl}amino)carbonyl]amino}propanoic acid | 0.05 | 100 |
| (3S)-3-(1,3-benzodioxol-5-yl)-3-{[({(1S)-2-methylsulfanyl)-1-[(phenylsulfanyl)methyl]ethyl}amino)carbonyl]amino}propanoic acid | 0.1 | 100 |
| N,N'-bis[(1S)-1-(1,3-benzodioxol-5-yl)-2-carboxyethyl]urea | 7 | 99 |
| (9S,13S)-13-(1,3-benzodioxol-5-yl)-9-[({4-[(2-methylbenzyl)amino]benzyl}amino)carbonyl]-3,11-dioxo-1-phenyl-2-oxa-4,10,12-triazapentadecan-15-oic acid | 0.0004 | 100 |
| (3S)-3-(1,3-benzodioxol-5-yl)-3-(((((1R)-2-(benzylfulsonyl)-1-((phenylsulfanyl)methyl)ethyl)amino)carbonyl)amino)propanoic acid | 1 | 100 |
| (3S)-3-(1,3-benzodioxol-5-yl)-3-{[({(1S)-1-[(phenylsulfanyl)methyl]pentyl}amino)carbonyl]amino}propanoic acid | 0.4 | 100 |
| (3S)-3-(1,3-benzodioxol-5-yl)-3-[({[(1S)-1-(1,3-benzodioxol-5-yl)-3-(tert-butoxy)-3-oxopropyl]amino}carbonyl)amino]propanoic acid | 4 | 100 |

TABLE 1-continued

| Compound | IC$_{50}$ | % A |
|---|---|---|
| (3S)-3-[({[(1S)-1-{[(2-aminophenyl)sulfanyl]methyl}-3-(methylsulfanyl)propyl]amino}carbonyl)amino]-3-(1,3-benzodioxol-5-yl)propanoic acid | 0.3 | 100 |
| (3S)-3-(1,3-benzodioxol-5-yl)-3-[({[(1S)-1-{[(2-methylphenyl)sulfanyl]methyl}-3-(methylsulfanyl)propyl]amino}carbonyl)amino]propanoic acid | 0.3 | 100 |
| (3S)-3-(1,3-benzodioxol-5-yl)-3-[({[(1S)-1-{[(3-methylphenyl)sulfanyl]methyl}-3-(methylsulfanyl)propyl]amino}carbonyl)amino]propanoic acid | 0.3 | 100 |
| (3S)-3-(1,3-benzodioxol-5-yl)-3-[({[2-(phenylsulfanyl)ethyl]amino}carbonyl)amino]propanoic acid | 6 | 100 |
| (3S)-3-(1,3-benzodioxol-5-yl)-3-{[({(1S)-2-[(3-phenylpropyl)sulfanyl]-1-[(phenylsulfanyl)methyl]ethyl}amino)carbonyl]amino}propanoic acid | 2 | 100 |
| (3S)-3-(1,3-benzodioxol-5-yl)-3-{[({(1S)-2-(phenylsulfanyl)-1-[(propylsulfanyl)methyl]ethyl}amino)carbonyl]amino}propanoic acid | 0.5 | 100 |
| (3S)-3-(1,3-benzodioxol-5-yl)-3-{[({(1S)-3-(methylsulfanyl)-1-[(phenylsulfanyl)methyl]propyl}amino)carbothioyl]amino}propanoic acid | 3 | 100 |
| (3S)-4-(methylsulfanyl)-3-{[({(1S)-3-(methylsulfanyl)-1-[(phenylsulfanyl)methyl]propyl}amino)carbonyl]amino}butanoic acid | 8 | 99 |
| (3S)-3-{[({(1S)-3-(methylsulfanyl)-1-[(phenylsulfanyl)methyl]propyl}amino)carbonyl]amino}-4-(phenylsulfanyl)butanoic acid, 8 | 4 | 100 |
| (3S)-3-(1,3-benzodioxol-5-yl)-3-[({[(1S)-1-methyl-2-(phenylsulfanyl)ethyl]amino}carbonyl)amino]propanoic acid | 3 | 100 |
| (3S)-3-(1,3-benzodioxol-5-yl)-3-{[({(1S)-2-(octylsulfanyl)-1-[(phenylsulfanyl)methyl]ethyl}amino)carbonyl]amino}propanoic acid | 5 | 98 |
| (3S)-3-(1,3-benzodioxol-5-yl)-3-{[({(1S)-3-(methylsulfanyl)-1-[({3-[(2-toluidinocarbonyl)amino]phenyl}sulfanyl)methyl]propyl}amino)carbonyl]amino}propanoic acid | 0.002 | 100 |
| (3S)-3-(1,3-benzodioxol-5-yl)-3-[({[(1S)-3-(methylsulfanyl)-1-(phenoxymethyl)propyl]amino}carbonyl)amino]propanoic acid | 20 | 100 |
| (3S)-3-(1,3-benzodioxol-5-yl)-3-{[(methyl{(1S)-3-(methylsulfanyl)-1-[(phenylsulfanyl)methyl]propyl}amino)carbonyl]amino}propanoic acid | 35 | 78 |
| (3S)-3-(1,3-benzodioxol-5-yl)-3-{[({1-[(phenylsulfanyl)methyl]pentyl}oxy)carbonyl]amino}propanoic acid | 6 | 100 |
| (3S)-3-(1,3-benzodioxol-5-yl)-3-{[({2-(phenylsulfanyl)-1-[(phenylsulfanyl)methyl]ethyl}amino)carbonyl]amino}propanoic acid | 1.5 | 99 |
| (3S)-3-(1,3-benzodioxol-5-yl)-3-{[({(1S)-2-[(carboxymethyl)sulfanyl]-1-[(phenylsulfanyl)methyl]ethyl}amino)carbonyl]amino}propanoic acid | 2 | 100 |
| (3S)-3-[({[(1S)-1-{[(3-aminophenyl)thio]methyl}-3-(methylthio)propyl]amino}carbonyl)amino]-3-(1,3-benzodioxol-5-yl)propanoic acid | 0.3 | 100 |
| (3S)-3-(1,3-benzodioxol-5-yl)-3-[({[(1S)-1-[(∴4-[(2-methylbenzyl)amino]phenyl}thio)methyl]-3-(methylthio)propyl]amino}carbonyl)amino]propanoic acid | 2 | 93 |
| (3S)-3-(1,3-benzodioxol-5-yl)-3-[({[(1S)-1-[({3-[(methylsulfonyl)amino]phenyl}thio)methy]-3-(methylthio)propyl]amino}carbonyl)amino]propanoic acid | 0.4 | 100 |
| (3S)-3-(1,3-benzodioxol-5-yl)-3-{[({(1S)-3-(methylthio)-1-[({3-(propylsulfonyl)amino]phenyl}thio)methyl]propyl}amino)carbonyl]amino}propanoic acid | 0.5 | 100 |
| (3S)-3-{[({(1S)-2-(allyloxy)-1-[(phenylthio)methyl]ethyl}amino)carbonyl]amino}-3-(1,3-benzodioxol-5-yl)propanoic acid | 0.3 | 100 |
| (3S)-3-(1,3-benzodioxol-5-yl)-3-{[({(1S)-2-(benzyloxy)-1-[(phenylthio)methyl]ethyl}amino)carbonyl]amino}propanoic acid | 0.3 | 100 |
| (3S)-3-(1,3-benzodioxol-5-yl)-3-[({[(1R)-1-phenyl-2-(propylthio)ethyl]amino}carbonyl)amino]propanoic acid | 25 | 100 |
| (3S)-3-(1,3-benzodioxol-5-y7l)-3-[({[(1R)-1-benzyl-2-(propylthio)ethyl]amino}carbonyl)amino]propanoic acid | 2 | 100 |
| (3S)-3-(1,3-benzodioxol-5-yl)-3-{[({(1S)-3-(phenylthio)-1-[(phenylthio)methyl]propyl}amino)carbonyl]amino}propanoic acid | 0.3 | 100 |
| (3S)-3-(1,3-benzodioxol-5-yl)-3-{[({(1S)-4-hydroxy-1-[(phenylthio)methyl]butyl}amino)carbonyl]amino}propanoic acid | 2 | 100 |
| (3S)-3-(1,3-benzodioxol-5-yl)-3-{[({(1S)-2-ethoxy-1-[(phenylthio)methyl]ethyl}oxy)carbonyl]amino}propanoic acid | 5 | 100 |
| (3S)-3-(1,3-benzodioxol-5-yl)-3-{[({(1S)-2-(phenethyloxy)-1-[(phenylthio)methyl]ethyl}oxy)carbonyl]amino}propanoic acid | 4 | 100 |
| (3S)-3-(1,3-benzodioxol-5-yl)-3-{[({(1S)-2-[(cyclopropylmethyl)thio]-1-[(phenylthio)methyl]ethyl}amino)carbonyl]amino}propanoic acid | 0.2 | 100 |
| (3S)-3-(1,3-benzodioxol-5-yl)-3-{[({(1R)-2-(benzyloxy)-1-[(benzylthio)methyl]ethyl}amino)carbonyl]amino}propanoic acid | 1 | 100 |
| (3S)-3-(1,3-benzodioxol-5-yl)-3-{[({(1R)-2-(benzyloxy)-1-[(benzylthio)methyl]ethyl}oxy)carbonyl]amino}propanoic acid | 10 | 100 |
| (3S)-3-(1,3-benzodioxol-5-yl)-3-{[({(1R)-2-(benzyloxy)-1-[(ethylthio)methyl]ethyl}oxy)carbonyl]amino}propanoic acid | 12 | 100 |
| (3S)-3-(1,3-benzodioxol-5-yl)-3-{[({(1S)-2-(ethylthio)-1-[(Phenylthio)methyl]ethyl}oxy)carbonyl]amino}propanoic acid | 1 | 100 |
| (3S)-3-(1,3-benzodioxol-5-yl)-3-{[({(1S)-2-(benzylthio)-1-[(phenylthio)methyl]ethyl}oxy)carbonyl]amino}propanoic acid | 3 | 100 |
| (3S)-3-(1,3-benzodixol-5-yl)-3-{[({(1S)-1-[({4-[(2-toluidinocarbonyl)amino]phenyl}thio)methyl]pentyl}oxy)carbonyl]amino}propanoic acid | 0.3 | 100 |
| (3S)-3-(1,3-benzodioxol-5-yl)-3-{[({(1S)-1-[({3-[(2-methylbenzyl)amino]phenyl}thio)methyl]pentyl}oxy)carbonyl]amino}propanoic acid, 15 | 25 | 100 |
| (3S)-3-(1,3-benzodioxol-5-yl)-3-{[({(1S)-2-{[(4-methylphenyl)sulfonyl]amino}-1-[(phenylthio)methyl]ethyl}amino)carbonyl]amino}propanoic acid | 10 | 98 |

TABLE 1-continued

| Compound | IC$_{50}$ | % A |
|---|---|---|
| (3S)-3-(1,3-benzodioxol-5-yl)-3-{[({(1S)-1-[(2-thienylmethoxy)methyl]pentyl}amino) carbonyl]amino}propanoic acid, 22 | 1.5 | 100 |

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

It is claimed:

1. A compound of the structure

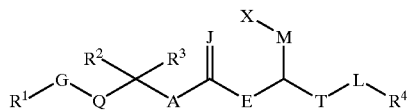

wherein A is selected from the group consisting of O, S, and NR$^5$;

E is selected from the group consisting of CH$_2$, O, S, and NR$^6$;

Q is selected from the group consisting of C(O) and (CH$_2$)$_k$ wherein k is an integer of 0 or 1;

J is selected from the group consisting of O, S and NR$^8$;

G is selected from the group consisting of O, NH, S, and (CH$_2$)$_p$ wherein p is an integer of 0 or 1;

T is selected from the group consisting of C(O) and (CH$_2$)$_b$ wherein b is an integer of from 0 to 3;

L is selected from the group consisting of O, NR$^7$, S, and (CH$_2$)$_n$ wherein n is an integer of 0 or 1;

M is selected from the group consisting of C(R$^9$)(R$^{10}$) and (CH$_2$)$_u$, wherein u is an integer of from 0 to 3;

X is selected from the group consisting of CO$_2$B, PO$_3$H$_2$, SO$_3$H, OPO$_3$H$_2$, C(O)NHC(O)R$^{11}$, C(O)NHSO$_2$R$^{12}$, tetrazolyl and hydrogen;

B, R$^1$, R$^2$, R$^3$, R$^4$, R$^5$, R$^6$, R$^7$, R$^8$, R$^9$, R$^{10}$, R$^{11}$ and R$^{12}$ are independently selected from the group consisting of hydrogen, alkyl, cycloalkyl, aryl, hydroxyalkyl, alkoxy, alkoxyalkoxy, cycloalkylalkyl, alkylamino, haloalkyl, alkylaryl, arylalkyl, heterocyclyl, alkylheterocyclyl and heterocyclylalkyl groups;

wherein R$^2$ and R$^3$ taken together may form a ring;

R$^4$ and R$^7$ taken together may form a ring;

R$^9$ and R$^{10}$ taken together may form a ring;

and salts thereof.

2. A compound of claim 1 wherein R$^1$, R$^2$ and R$^3$ are independently selected from the group consisting of hydrogen, alkoxy, alkoxyalkoxy, aryl, alkylaryl, arylalkyl, heterocyclyl and alkyl;

R$^4$ is selected from the group consisting of aryl, alkylaryl, arylalkyl, heterocyclyl, alkylheterocyclyl and heterocyclylalkyl;

X is CO$_2$B; and

M is C(R$^9$)(R$^{10}$) wherein R$^9$ and R$^{10}$ are independently selected from the group consisting of hydrogen and lower alkyl.

3. A compound of claim 1 further comprising derivatives of said compound selected from the group consisting of esters, carbamates, aminals, and amides, thereof.

4. A compound of claim 1 of the structure

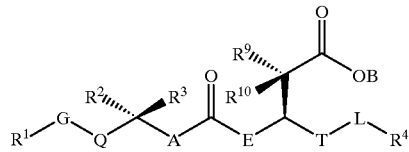

wherein A is selected from the group consisting of O, S, and NR$^5$;

E is selected from the group consisting of CH$_2$, O, S, and NR$^6$;

Q is selected from the group consisting of C(O) and (CH$_2$)$_k$ wherein k is an integer of 0 or 1;

G is selected from the group consisting of O, NH, S, and (CH$_2$)$_p$ wherein p is an integer of 0 or 1;

T is selected from the group consisting of C(O) and (CH$_2$)$_b$ wherein b is an integer of 0 to 3;

L is selected from the group consisting of O, NR$^7$, S, and (CH$_2$)$_n$ wherein n is an integer of 0 or 1;

B, R$^1$, R$^2$, R$^3$, R$^4$, R$^5$, R$^6$, R$^7$, R$^9$ and R$^{10}$ are independently selected from the group consisting of hydrogen, alkyl, cycloalkyl, aryl, hydroxyalkyl, alkoxy, alkoxyalkoxy, cycloalkylalkyl, alkylamino, haloalkyl, alkylaryl, arylalkyl, heterocyclyl, alkylheterocyclyl and heterocyclylalkyl groups;

wherein R$^2$ and R$^3$ taken together may form a ring;

R$^4$ and R$^7$ taken together may form a ring;

R$^9$ and R$^{10}$ taken together may form a ring;

and salts thereof.

5. A compound of claim 4 wherein R$^1$, R$^2$ and R$^3$ are independently selected from the group consisting of hydrogen, alkoxy, alkoxyalkoxy, aryl, alkylaryl, arylalkyl, heterocyclyl and alkyl;

R$^4$ is selected from the group consisting of aryl, alkylaryl, arylalkyl, heterocyclyl, heterocyclylalkyl and alkyheterocyclyl;

R$^5$ and R$^6$ are hydrogen; and

R$^9$ and R$^{10}$ are independently selected from the group consisting of hydrogen and lower alkyl.

6. A compound of claim 4 further comprising derivatives of said compound selected from the group consisting of esters, carbamates, aminals, and amides, thereof.

7. A compound of claim 1 selected from the group consisting of: (3S)-3-(1,3-benzodioxol-5-yl)-3-(((((1S)-3-(methylsulfanyl)-1-((phenylsulfanyl)methyl)propyl)amino) carbonyl)amino)propanoic acid, (3S)-3-(1,3-benzodioxol-5-yl)-3-(((((1S)-2-((cyclopropylmethyl)thio)-1-((phenylthio) methyl)ethyl)amino)carbonyl)amino)propanoic acid, (9S, 13S)-13-(1,3-benzodioxol-5-yl)-3,11-dioxo-1-phenyl-9-{

[(2-thienylmethyl)amino]carbonyl}-2-oxa-4,10,12-triazapentadecan-15-oic acid, (9S,13S)-13-(1,3-benzodioxol-5-yl)-9-{[(3-hydroxy-4-methoxybenzyl)amino]carbonyl}-3,11-dioxo-2-oxa-4,10,12-triazapentadecan-15-oic acid, (3S)-3-(1,3-benzodioxol-5-yl)-3-{[({(1S)-2-(benzylsulfanyl)-1-[(phenylsulfanyl)methyl]ethyl}amino)carbonyl]amino}propanoic acid, (3S)-3-(1,3-benzodioxol-5-yl)-3-{[({(1S)-3-(methylsulfanyl)-1-[({4-[(2-toluidinocarbonyl)amino]phenyl}sulfanyl) methyl]propyl}amino)carbonyl]amino}propanoic acid, (3S)-3-(1,3-benzodioxol-5-yl)-3-{[({(1S)-2-(ethylsulfanyl)-1-[(phenylsulfanyl)methyl]ethyl}amino) carbonyl]amino}propanoic acid, (9S,13S)-13-(1,3-benzodioxol-5-yl)-9-[({4-[(2-methylbenzyl)amino]benzyl}amino)carbonyl]-3,11-dioxo-1-phenyl-2-oxa-4,10,12-triazapentadecan-15-oic acid, (3S)-3-(1,3-benzodioxol-5-yl)-3-{[({(1S)-3-(methylsulfanyl)-1-[({3-[(2-toluidinocarbonyl)amino]phenyl}sulfanyl)methyl]propyl}amino)carbonyl]amino}propanoic acid, (3S)-3-(1,3-benzodioxol-5-yl)-3-{[({(1S)-2-(ethylthio)-1-[(phenylthio)methyl]ethyl}oxy)carbonyl]amino}propanoic acid, (9S,13S)-13-(1,3-benxodioxol-5-yl)-3,11-dioxo-1-phenyl-9-(((4-((2-toluidinocarbonyl)amino)benzyl)amino)carbonyl)-$^2$-oxa-4,10,12-triazapentadecan-15-oic acid, and pharmaceutically acceptable salts thereof.

8. A compound of claim 7 further comprising derivatives of said compound selected from the group consisting of esters, carbamates, aminals, amides, and optical isomers thereof.

9. A pharmaceutical composition comprising:

a compound of claim 1 and pharmaceutically acceptable salts thereof, in a pharmaceutically acceptable carrier.

10. A method for selectively inhibiting $\alpha_4\beta_1$ integrin binding in a mammal comprising administering to said mammal a therapeutic amount of a compound of claim 1.

* * * * *

UNITED STATES PATENT AND TRADEMARK OFFICE
CERTIFICATE OF CORRECTION

PATENT NO. : 6,096,773
DATED : August 1, 2000
INVENTOR(S) : Ian L. Scott et al.

It is certified that error appears in the above-identified patent and that said Letters Patent is hereby corrected as shown below:

Column 4,
Line 3, please delete "expresses" and -- expresses $\alpha_4\beta_1$. --
Line 42, please delete "$R_bO$-RCO-" and insert -- $R_bO$-$R_cO$- --
Line 44, please delete "$(CH_2)_n$" and insert -- $(CH_2)_{n'}$ --

Column 5,
Line 51, please delete "such" and insert -- such as --

Column 13,
Line 1, please delete "quatemized" and insert -- quaternized --

Column 14,
Line 35, please delete "intracistemally" and insert -- intracisternally --
Line 39, please delete "intrastemal" and insert -- intrasternal --

Column 17,
Line 27, please delete "formns" and insert -- forms --

Column 19,
Line 6, please delete "added hydrochloric acid" and insert -- added to hydrochloric acid --

Column 20,
Line 11, please delete "added by dropwise" and insert -- added dropwise --

Column 23,
Line 62, please delete "(methylsulfanyl)propyl]aminol}carbonyl)amino]-3-(1,3-"
and insert -- (methylsulfanyl)propyl]amino}carbonyl)amino]-3-(1,3- --
Table 1,
Entry 39, please delete "3-{[({(1S)-3-(methylsulfanyl)-1- [(phenylsulfanyl)methyl] propyl}amino)propanoic amino}propanoic acid" and insert -- 3-{[({(1S)-3-(methylsulfanyl)-1-[phenylsulfanyl)methyl]propyl}amino)carbonyl]amino}propanic acid --
Entry 41, please delete "(2)-2-({[((1S)-5-{[(benzyloxy)carbonyl}amino}1-1{[(2-thienylmethyl)amino]carbonyl}pentyl)amino]carbonyl}amino)butanedioic acid"
and insert -- (2S)-2({[((1S)-5-{[benzyloxy)carbonyl}amino}1-1{[(2-thienylmethyl) amino] carbonyl}pentyl)amino]carbonyl}amino}1-1{[(2-thienylmethyl)amino] carbonyl}pentyl)amino]carbonyl}amino)butanedioic acid --

UNITED STATES PATENT AND TRADEMARK OFFICE
CERTIFICATE OF CORRECTION

PATENT NO. : 6,096,773
DATED : August 1, 2000
INVENTOR(S) : Ian L. Scott et al.

It is certified that error appears in the above-identified patent and that said Letters Patent is hereby corrected as shown below:

Table 1,
Entry 67, please delete "(3S)-3-(1,3-benzodioxol-5yl)-3-[({[(1S)-1[([: (4-[2-methylbenzyl)amino]phenyl}thio)methyl]-3-(methylthio)propyl]amino}carbonyl) amino]propanic acid" and insert -- 3(S)-3-(1,3-benzodioxol-5yl)-3-[({[(1S)-1-[({4-[(2-methylbenzyl)amino]phenyl}thio)methyl]-3-(methylthio)propyl]amino}carbonyl) amino]propanic acid --
Entry 73, please delete "(3S)-3-(1,3-benzodioxol-5-y71)-3-[({[(1R)-1-benzyl-2-(propylthio)ethyl]amino}carbonyl)amino]propanic acid" and insert -- (3S)-3-(1,3-benzodioxol-5-yl)-3-[({[(1R)-1-(benzyl-2-(propylthio)ethyl]amino}carbonyl)amino] propanic acid --
Entry 82, please delete "(3S)-3-(1,3-benzoldioxol-5-yl)-3-{[({1S)-2-(ethylthio)-1-[(Phenlthio)methyl]ethyl}oxy)carbonyl]amino}propanic acid" and insert -- (3S)-3-(1,3-benzoldioxol-5-yl)-3-{[({(1S)-2-(ethylthio)-1-[(phyenlthio) methyl]ethyl}oxy) carbonyl]amino}propanic acid --

Column 34,
Line 2, please delete "benxodioxol-5-yl)-3" and insert -- benzodioxol-5-yl)-3 --
Line 3, please delete "-²-oxa-4" and insert -- -2-oxa--4 --

Signed and Sealed this

Twelfth Day of February, 2002

*Attest:*

*Attesting Officer*

JAMES E. ROGAN
*Director of the United States Patent and Trademark Office*

(12) EX PARTE REEXAMINATION CERTIFICATE (6435th)
United States Patent
Scott et al.

(10) Number: US 6,096,773 C1
(45) Certificate Issued: Sep. 16, 2008

(54) COMPOUNDS THAT INHIBIT THE BINDING OF INTEGRINS TO THEIR RECEPTORS

(75) Inventors: Ian L. Scott, Albany, NY (US); Bore G. Raju, Fremont, CA (US); Ronald J. Biediger, Houston, TX (US); Vanessa O. Grabbe, Sugar Land, TX (US); Jamal Kassir, Houston, TX (US); Karin M. Keller, Houston, TX (US); Timothy P. Kogan, deceased, late of Sugar Land, TX (US); by Patricia Woodard Kogan, legal representative, Sugar Land, TX (US); Shuqun Lin, Huntingdon Valley, PA (US); Robert V. Market, Pearland, TX (US)

(73) Assignee: Encysive Pharmaceuticals Inc., Houston, TX (US)

Reexamination Request:
No. 90/008,431, Jan. 17, 2007

Reexamination Certificate for:
Patent No.: 6,096,773
Issued: Aug. 1, 2000
Appl. No.: 09/292,459
Filed: Apr. 15, 1999

Certificate of Correction issued Feb. 12, 2002.

Related U.S. Application Data
(60) Provisional application No. 60/082,019, filed on Apr. 16, 1998.

(51) Int. Cl.
| | | |
|---|---|---|
| C07D 405/00 | (2006.01) | |
| C07D 417/14 | (2006.01) | |
| C07D 405/14 | (2006.01) | |
| C07D 317/60 | (2006.01) | |
| C07D 409/12 | (2006.01) | |
| C07D 409/14 | (2006.01) | |
| C07D 413/00 | (2006.01) | |
| C07D 317/00 | (2006.01) | |
| C07D 333/00 | (2006.01) | |
| C07D 413/14 | (2006.01) | |
| C07D 409/00 | (2006.01) | |
| C07D 333/20 | (2006.01) | |
| C07D 333/24 | (2006.01) | |
| C07D 417/00 | (2006.01) | |

(52) U.S. Cl. ............ 514/382; 514/444; 514/467; 514/512; 514/557; 548/252; 549/60; 549/74; 549/76; 549/78; 549/452; 549/550; 560/17; 560/22; 562/431; 564/163

(58) Field of Classification Search .................. None
See application file for complete search history.

(56) References Cited

U.S. PATENT DOCUMENTS
| | | |
|---|---|---|
| 3,936,452 A | 2/1976 | Nagasawa et al. |
| 5,830,869 A | 11/1998 | Mitchell et al. |

FOREIGN PATENT DOCUMENTS
| | | |
|---|---|---|
| EP | 0 226 304 A1 | 10/1986 |
| WO | WO 98/04247 | 2/1998 |

OTHER PUBLICATIONS

Marseigne, I., et al., Full Agonists of CCK8 Containing a Nonhydrolyzable Sulfated Tyrosine Residue, *Journal of Medicinal Chemistry*, 32(2), 445–449 (1989).

Chough, Yun Sung, et al., Synthetic Studies of 2,2'–(ethylenediimino) and 2,2'–(thioureido) dicarboxylic acids as Antitubercular and the Other Bacteriostatic Agents, Yakhak Hoji, 10(2–3), 8–11 (1966).

*Primary Examiner*—Evelyn Huang

(57) ABSTRACT

A method for the inhibition of the binding of $\alpha_4\beta_1$ integrin to its receptors, for example VCAM-1 (vascular cell adhesion molecule-1) and fibronectin; compounds that inhibit this binding; pharmaceutically active compositions comprising such compounds; and the use of such compounds either as above, or in formulations for the control or prevention of diseases states in which $\alpha_4\beta_1$ is involved.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3 and 6 are cancelled.

Claims 1–2, 4–5 and 7 are determined to be patentable as amended.

New Claims 11–13 are added and determined to be patentable.

Claims 8–10 were not reexamined.

1. A compound of the structure

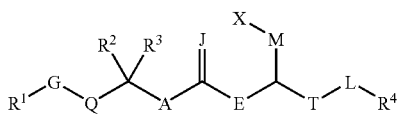

wherein A is selected from the group consisting of O, S, and NR$^5$;

E is selected from the group consisting of CH$_2$, O, S, and NR$^6$;

Q is selected from the group consisting of C(O) and (CH$_2$)$_k$ wherein k is an integer of 0 or 1 ;

J is selected from the group consisting of O, S and NR$^8$;

G is selected from the group consisting of O, NH, S, and (CH$_2$)$_p$ wherein p is an integer of 0 or 1 ;

T is selected from the group consisting of C(O) and (CH$_2$)$_b$ wherein b is an integer of from 0 to 3 ;

L is selected from the group consisting of O, NR$^7$, S, and (CH$_2$)$_n$ wherein n is an integer of 0 or 1 ;

M is selected from the group consisting of C(R$^9$)(R$^{10}$) and (CH$_2$)$_u$, wherein u is an integer of from 0 to 3 ;

X is selected from the group consisting of CO$_2$B, PO$_3$H$_2$, SO$_3$H, OPO$_3$H$_2$, C(O)NHC(O)R$^{11}$, C(O)NHSO$_2$R$^{12}$, tetrazolyl and hydrogen;

B, [R$^1$, R$^2$, R$^3$, R$^4$,] R$^5$, R$^6$, R$^7$, R$^8$, R$^9$, R$^{10}$, R$^{11}$ and R$^{12}$ are independently selected from the group consisting of hydrogen, alkyl, cycloalkyl, aryl, hydroxyalkyl, alkoxy, alkoxyalkoxy, cycloalkylalkyl, alkylamino, haloalkyl, alkylaryl, arylalkyl, heterocyclyl, alkylheterocyclyl and heterocyclylalkyl groups;

*R$^1$ and R$^2$ are independently selected from the group consisting of phenyl, thienylmethyl, isobutyl, n-butyl, 2-thienylmethyl, 1,3-thiazol-2ylmethyl, benzyl, thienyl, 3-pyrimidinylmethyl, 3-methyl-1-benzothiophen-2-yl, allyl, isobutyl, 3-methozybenzyl, propyl, 2-ethoxyethyl, cyclopropylmethyl, benzylsulfanylmethyl, phenylsulfonylmethyl, phenethylsulfanylmethyl, 3-phenylpropylsuflanylmethyl, 4-((2-toluidocarbonyl) amino)benzyl, 2-pyridinylethyl, 2-(1H-indol-3-yl)ethyl, 1H-benzimidazol-2-yl, 4-piperidinylmethyl, 3-hydroxy-4-methoxybenzyl, 4-hydroxyphenethyl, 4-aminobenzyl, phenylsulfonylmethyl, 4-(acetylamino)phenyl, 4-methoxyphenyl, 4-aminophenyl, 4-chlorophenyl, (4-benzylsulfonyl)amino)phenyl, (4-(methylsulfonyl) amino)phenyl, 2-aminophenyl, 2-methylphenyl, isopropyl, 2-oxo-1-pyrrolidinyl, 3-(methylsulfanyl) propyl, (propylsulfanyl)methyl, (octylsulfanyl)methyl, 3-aminophenyl, 4-((2-toluidinocarbonyl)amino) phenyl, 2-((methylbenzyl)amino)benzyl, (methylsulfanyl)ethyl, and (ethylsulfanyl)methyl;*

*R$^3$ is selected from the group consisting of hydrogen, phenyl, thienylmethyl, isobutyl, n-butyl, 2-thienylmethyl, 1,3-thiazol-2ylmethyl, benzyl, thienyl, 3-pyrimidinylmethyl, 3-methyl-1-benzothiophen-2-yl, allyl, isobutyl, 3-methozybenzyl, propyl, 2-ethoxyethyl, cyclopropylmethyl, benzylsulfanylmethyl, phenylsulfonylmethyl, phenethylsulfanylmethyl, 3-phenylpropylsuflanylmethyl, 4-((2-toluidocarbonyl) amino)benzyl, 2-pyridinylethyl, 2-(1H-indol-3-yl)ethyl, 1H-benzimidazol-2-yl, 4-piperidinylmethyl, 3-hydroxy-4-methoxybenzyl, 4-hydroxyphenethyl, 4-aminobenzyl, phenylsulfonylmethyl, 4-(acetylamino)phenyl, 4-methoxyphenyl, 4-aminophenyl, 4-chlorophenyl, (4-benzylsulfonyl)amino)phenyl, (4-(methylsulfonyl) amino)phenyl, 2-aminophenyl, 2-methylphenyl, isopropyl, 2-oxo-1-pyrrolidinyl, 3-(methylsulfanyl) propyl, (propylsulfanyl)methyl, (octylsulfanyl)methyl, 3-aminophenyl, 4-((2-toluidinocarbonyl)amino) phenyl, 2-((methylbenzyl)amino)benzyl, (methylsulfanyl)ethyl, and (ethylsulfanyl)methyl;*

*R$^4$ is selected from the group consisting of 1,3-benzodioxol-5-yl, 1-naphthyl, thienyl, 4-isobutyoxyphenyl, 2,6-dimethylphenyl, allyoxyphenyl, 3-bromo-4-methoxyphenyl, 4-butoxyphenyl, 1-benzofuran-2-yl, 2-thienylmethyl, phenyl, methylsulfanyl, phenylsulfanyl, phenethylsulfanyl, 4-bromo-2-thienyl, 3-methyl-2-thienyl and 4,5-dihydro-1,3-oxazol-2-yl;* wherein R$^2$ and R$^3$ taken together may form a ring;

R$^4$ and R$^7$ taken together may form a ring;

R$^9$ and R$^{10}$ taken together may form a ring; and salts, esters, carbamates, aminals, and amides thereof.

2. A compound of claim 1 wherein [R$^1$, R$^2$ and R$^3$ are independently selected from the group consisting of hydrogen, alkoxy, alkoxyalkoxy, aryl, alkylaryl, arylalkyl, heterocyclyl and alkyl;]

[R$^4$ is selected from the group consisting of aryl, alkylaryl, arylalkyl, heterocyclyl, alkylheterocyclyl and heterocyclylalkyl;]

X is CO$_2$B; and

M is C(R$^9$)(R$^{10}$) wherein R$^9$ and R$^{10}$ are independently selected from the group consisting of hydrogen and lower alkyl.

4. A compound of claim 1 of the structure

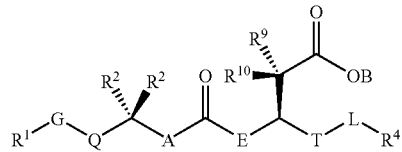

wherein A is selected from the group consisting of O, S, and NR$^5$;

3

E is selected from the group consisting of CH$_2$, O, S, and NR$^6$;

Q is selected from the group consisting of C(O) and (CH$_2$)$_k$ wherein k is an integer of 0 or 1;

G is selected from the group consisting of O, NH, S, and (CH$_2$)$_p$ wherein p is an integer of 0 or 1;

T is selected from the group consisting of C(O) and (CH$_2$)$_b$ wherein b is an integer of 0 or 3;

L is selected from the group consisting of O, NR$^7$, S, and (CH$_2$)$_n$ wherein n is an integer of 0 or 1;

B, [R$^1$, R$^2$, R$^3$, R$^4$,] R$^5$, R$^6$, R$^7$, R$^9$ and R$^{10}$ are independently selected from the group consisting of hydrogen, alkyl, cycloalkyl, aryl, hydroxyalkyl, alkoxy, alkoxyalkoxy, cycloalkylalkyl, alkylamino, haloalkyl, alkylaryl, arylalkyl, heterocyclyl, alkylheterocyclyl and heterocyclylalkyl groups;

*R$^1$ and R$^2$ are independently selected from the group consisting of phenyl, thienylmethyl, isobutyl, n-butyl, 2-thienylmethyl, 1,3-thiazol-2ylmethyl, benzyl, thienyl, 3-pyrimidinylmethyl, 3-methyl-1-benzothiophen-2-yl, allyl, isobutyl, 3-methozybenzyl, propyl, 2-ethoxyethyl, cyclopropylmethyl, benzylsulfanylmethyl, benzylsulfanylmethyl, phenylsulfonylmethyl, phenethylsulfanylmethyl, 3-phenylpropylsuflanylmethyl, 4-((2-toluidocarbonyl) amino)benzyl, 2-pyridinylethyl, 2-(1H-indol-3-yl)ethyl, 1H-benzimidazol-2-yl, 4-piperidinylmethyl, 3-hydroxy-4-methoxybenzyl, 4-hydroxyphenethyl, 4-aminobenzyl, phenylsulfonylmethyl, 4-(acetylamino)phenyl, 4-methoxyphenyl, 4-aminophenyl, 4-chlorophenyl, (4-benzylsulfonyl)amino)phenyl, (4-(methylsulfonyl) amino)phenyl, 2-aminophenyl, 2-methylphenyl, isopropyl, 2-oxo-1-pyrrolidinyl, 3-(methylsulfanyl) propyl, (propylsulfanyl)methyl, (octylsulfanyl)methyl, 3-aminophenyl, 4-((2-toluidinocarbonyl) amino) phenyl, 2-((methylbenzyl)amino)benzyl, (methylsulfanyl)ethyl, and (ethylsulfanyl)methyl;*

*R$^3$ is selected from the group consisting of hydrogen, phenyl, thienylmethyl, isobutyl, n-butyl, 2-thienylmethyl, 1,3-thiazol-2ylmethyl, benzyl, thienyl, 3-pyrimidinylmethyl, 3-methyl-1-benzothiophen-2-yl, allyl, isobutyl, 3-methozybenzyl, propyl, 2-ethoxyethyl, cyclopropylmethyl, benzylsulfanylmethyl, benzylsulfanylmethyl, phenylsulfonylmethyl, phenethylsulfanylmethyl, 3-phenylpropylsuflanylmethyl, 4-((2-toluidocarbonyl) amino)benzyl, 2-pyridinylethyl, 2-(1H-indol-3-yl)ethyl, 1H-benzimidazol-2- yl, 4-piperidinylmethyl, 3-hydroxy-4-methoxybenzyl, 4-hydroxphenethyl, 4-aminobenzyl, phenylsulfonylmethyl, 4-(acetylamino) phenyl, 4-methoxyphenyl, 4-aminophenyl, 4-chlorophenyl, (4-benzylsulfonyl)amino)phenyl, (4-(methylsulfonyl)amino)phenyl, 2-aminophenyl, 2-methylphenyl, isopropyl, 2-oxo-1-pyrrolidinyl, 3-(methylsulfanyl)propyl, (propylsulfanyl)methyl, (octylsulfanyl)methyl, 3-aminophenyl, 4-((2-toluidinocarbonyl)amino)phenyl, 2-((methylbenzyl) amino)benzyl, (methylsulfanyl)ethyl, and (ethylsulfanyl)methyl;*

*R$^4$ is selected from the group consisting of 1,3-benzodioxol-5-yl, 1-naphthyl, thienyl, 4-isobutyoxyphenyl, 2,6-dimethylphenyl, allyoxyphenyl, 3-bromo-4-methoxyphenyl, 4-butoxyphenyl, 1-benzofuran-2-yl, 2-thienylmethyl,*

4

*phenyl, methylsulfanyl, phenylsulfanyl, phenethylsulfanyl, 4-bromo-2-thienyl, 3-methyl-2-thienyl and 4,5-dihydro-1,3-oxazol-2-yl;* wherein R$^2$ and R$^3$ taken together may form a ring;

R$^4$ and R$^7$ taken together may form a ring;

R$^9$ and R$^{10}$ taken together may form a ring; and, salts, *esters, carbamates, aminals, and amides* thereof.

5. A compound of claim 4 wherein

[R$^1$, R$^2$ and R$^3$ are independently selected from the group consisting of hydrogen, alkoxy, alkoxyalkoxy, aryl, alkylaryl, arylalkyl, heterocyclyl and alkyl;

[R$^4$ is selected from the group consisting of aryl, alkylaryl, arylalkyl, heterocyclyl, heterocyclylalkyl and alkyheterocyclyl;]

R$^5$ and R$^6$ are hydrogen; and

R$^9$ and R$^{10}$ are independently selected from the group consisting of hydrogen and lower alkyl.

7. A compound [of claim 1] selected from the group consisting of: (3S)-3-(1,3-benzodioxol-5-yl)-3-(((((1S)-3-(methylsulfanyl)-1- ((phenylsulfanyl)methyl)propyl)amino) carbonyl)amino)propanoic acid, (3S)-3-(1,3-benzodioxol-5-yl)-3-(((((1S)-2-((cyclopropylmethyl)thio)-1- ((phenylthio)methyl)ethyl)amino)carbonyl)amino)propanoic acid, (9S, 13S)-13-(1,3-benzodioxol-5-yl)-3,11-dioxo-1-phenyl-9[[2-thienylmethyl)amino]carbonyl]-2-oxa-4,10,12-triazapentadecan-15-ole acid, (9S,13S)- 13-(1,3-benzodioxol-5-yl)-9-{[(3-hydroxy-4-methoxybenzyl) amino]carbonyl}-3,11- dioxo-2-oxa-4,10,12-triazapentadecan-15-oic acid, (3S)-3-(1,3-benzodioxol-5-yl)-3-{[({1S)-2-(benzylsulfanyl)-1- [(phenylsulfanyl)methyl]ethyl}amino)carbonyl]amino}propanoic acid, (3S)-3-(1,3-benzodioxol-5-yl)-3-{[({1S)-3-(methylsulfanyl)-1-[({4-[(2- toluidinocarbonyl)amino]phenyl]sulfanyl) methyl]propyl}amino)carbonyl]amino]propanoic acid, (3S)-3-(1,3-benzodioxol-5-yl)-3- {([({1S)-2-(ethylsulfanyl)-1-[(phenylsulfanyl)methyl]ethyl}amino) carbonyl] amino}propanoic acid, (9S, 13S)-13-(1,3-benzodioxol-5-yl)-9-[({4-[2-methylbenzyl)amino]benzyl}amino) carbonyl]-3,11-dioxo-1-phenyl-2-oxa-4,10,12-trazapentadecan-15-oic acid, (3S)-3-(1,3-benzodioxol-5-yl)-3-{[({1S)-3-(methylsulfanyl)-1-[({3-[(2-toluidinocarbonyl)amino]phenyl}sulfanyl)methyl] propyl}amino)carbonyl]amino}propanic acid, (3S)-3-(1,3-benzodioxol-5-yl)-3-{[({1S)-2-(ethylthio)-1- [(phenylthio) methyl]ethyl}oxy)carbonyl]amino}propanoic acid, (9S, 13S)-13-(1,3-benzodioxol-5-yl)-3,11-dioxo-1-phenyl-9-(((4-((2- toluidinocarbonyl)amino)benzyl)amino)carbonyl)-2-oxa-4,10,12-triazapentadecan-15- oic acid, and pharmaceutically acceptable salts thereof.

*11. A compound of claim 1 wherein*

*R$^2$ and R$^3$ are linked to form a ring selected from the group consisting of cyclopropyl, cyclobutyl, cyclopentyl, cyclohexyl, 4-piperidinyl and 4-tetrahydropyranyl.*

*12. A compound of claim 1 wherein*

*R$^4$ and R$^7$ are linked to form a ring selected from the group consisting of 1-pyrrolidino, 1-piperidino, 4-methyl-1-piperizino, 4-acetyl-1-piperizino and 4-morpholino.*

*13. A compound of claim 1 wherein*

*R$^9$ and R$^{10}$ are linked to form a ring selected from the group consisting of cyclopropyl, cyclobutyl, cyclopentyl and cyclohexyl.*

\* \* \* \* \*